(12) United States Patent
Tegels

(10) Patent No.: US 11,039,921 B2
(45) Date of Patent: Jun. 22, 2021

(54) SEQUENTIAL DELIVERY OF TWO-PART PROSTHETIC MITRAL VALVE

(71) Applicant: Tendyne Holdings, Inc., St. Paul, MN (US)

(72) Inventor: Zachary J. Tegels, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 258 days.

(21) Appl. No.: 16/305,113

(22) PCT Filed: Jun. 12, 2017

(86) PCT No.: PCT/US2017/736949
§ 371 (c)(1),
(2) Date: Nov. 28, 2018

(87) PCT Pub. No.: WO2017/218375
PCT Pub. Date: Dec. 21, 2017

(65) Prior Publication Data
US 2019/0321178 A1 Oct. 24, 2019

Related U.S. Application Data

(60) Provisional application No. 62/349,418, filed on Jun. 13, 2016.

(51) Int. Cl.
*A61F 2/24* (2006.01)
*A61B 17/04* (2006.01)

(52) U.S. Cl.
CPC .......... *A61F 2/2439* (2013.01); *A61F 2/2409* (2013.01); *A61F 2/2418* (2013.01);
(Continued)

(58) Field of Classification Search
CPC .... A61F 2/2439; A61F 2/2409; A61F 2/2418; A61F 2/2436; A61F 2220/0075;
(Continued)

(56) References Cited

U.S. PATENT DOCUMENTS 2,697,008 A   12/1954   Ross
3,409,013 A   11/1968   Berry
(Continued)

FOREIGN PATENT DOCUMENTS

CN   1486161 A   3/2004
CN   1961845 A   5/2007
(Continued)

OTHER PUBLICATIONS

US 9,155,620 B2, 10/2015, Gross et al. (withdrawn)
(Continued)

*Primary Examiner* — Katrina M Stransky
(74) *Attorney, Agent, or Firm* — Lerner, David, Littenberg, Krumholz & Mentlik, LLP

(57) ABSTRACT

Apparatus and methods are described herein for use in the transvascular delivery and deployment of a prosthetic mitral valve. In some embodiments, an apparatus includes a prosthetic heart valve that includes an inner frame and an outer frame couplable to the inner frame via sutures. The prosthetic heart valve is movable between a first configuration for delivery and a second configuration when implanted in a heart. When in the first configuration, the inner frame can be disposed axially proximal of the outer frame and loosely coupled together via the sutures. When in the second configuration, the inner frame and outer frame are disposed in a nested configuration and can be secured together with the sutures. In some embodiments, the sutures are secured with
(Continued)

slip knots. In some embodiments, a delivery device can be used to secure the slip knots and sutures to the prosthetic valve.

23 Claims, 16 Drawing Sheets

(52) U.S. Cl.
CPC ........ *A61F 2/2436* (2013.01); *A61B 17/0467* (2013.01); *A61B 2017/0475* (2013.01); *A61F 2220/0075* (2013.01); *A61F 2250/0063* (2013.01)

(58) Field of Classification Search
CPC ............ A61F 2250/0063; A61F 2/2427; A61F 2/2433; A61B 17/0467
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |

(56) References Cited

U.S. PATENT DOCUMENTS

| | | | |
|---|---|---|---|
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |

(56) References Cited

U.S. PATENT DOCUMENTS

| | | |
|---|---|---|
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Bolen et al. |
| 8,945,208 B2 | 2/2015 | Jimenez et al. |
| 8,956,407 B2 | 2/2015 | Macoviak et al. |
| 8,961,597 B2 | 2/2015 | Subramanian et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,468,526 B2 | 10/2016 | Subramanian et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,327,894 B2 | 6/2019 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0069593 A1 | 4/2003 | Tremulis et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137690 A1 | 6/2005 | Salahieh et al. |

(56) References Cited

U.S. PATENT DOCUMENTS

| | | |
|---|---|---|
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074484 A1 | 4/2006 | Huber |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0195185 A1* | 8/2006 | Lane ............... A61F 2/2412 623/2.38 |
| 2006/0229708 A1 | 10/2006 | Powell |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Randert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1* | 1/2007 | Gurskis ............. A61F 2/2436 623/2.11 |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc |
| 2008/0091264 A1 | 4/2008 | Machold et al. |
| 2008/0109069 A1 | 5/2008 | Coleman et al. |
| 2008/0114442 A1 | 5/2008 | Mitchell et al. |
| 2008/0125861 A1 | 5/2008 | Webler et al. |
| 2008/0140189 A1 | 6/2008 | Nguyen et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |

(56) References Cited

U.S. PATENT DOCUMENTS

| | | |
|---|---|---|
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1 | 1/2010 | Seguin et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1 | 5/2010 | Subramanian et al. |
| 2010/0121437 A1 | 5/2010 | Subramanian et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1 | 9/2011 | Garrison et al. |
| 2011/0218619 A1* | 9/2011 | Benichou ............ A61F 2/2418 623/2.11 |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0010700 A1 | 1/2012 | Spenser |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0109079 A1 | 5/2012 | Asleson et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1 | 9/2012 | Solem |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1 | 4/2013 | Subramanian et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1 | 8/2013 | Yellin et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | McLean et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338764 A1 | 12/2013 | Thornton et al. |
| 2014/0005778 A1 | 1/2014 | Buchbinder et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1 | 12/2014 | Gorman, III et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |

(56) References Cited

U.S. PATENT DOCUMENTS

| | | | |
|---|---|---|---|
| 2015/0223934 A1 | 8/2015 | Vidlund et al. |
| 2015/0223935 A1 | 8/2015 | Subramanian et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100245 A1 | 4/2017 | Subramanian et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102791223 A | 11/2012 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001056512 A1 | 8/2001 |
| WO | 2001061289 A1 | 8/2001 |
| WO | 2001076510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A1 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |

(56) References Cited

FOREIGN PATENT DOCUMENTS

| | | |
|---|---|---|
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013/028387 A2 | 2/2013 |
| WO | 2013045262 A1 | 4/2013 |
| WO | 2013059747 A1 | 4/2013 |
| WO | 2013096411 A1 | 6/2013 |
| WO | 2013116785 A1 | 8/2013 |
| WO | 2013175468 A2 | 11/2013 |
| WO | 2014121280 A2 | 8/2014 |
| WO | 2014144020 A1 | 9/2014 |
| WO | 2014144937 A2 | 9/2014 |
| WO | 2014162306 A2 | 10/2014 |
| WO | 2014189974 A1 | 11/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http://webdocs.cs.ualberta.ca/~database/MEMS/sma.html>, Feb. 5, 2016, 3 pages.
International Search Report and Written Opinion for International Application No. PCT/US2016/016567, dated Aug. 3, 2016, 17 pages.
U.S. Pat. No. 9,155,620, Oct. 2015, Gross et al. (withdrawn).
Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.
Chinese Search Report for CN Application No. 201680013223.9, dated Oct. 29, 2018.
International Search Report and Written Opinion for International Application No. PCT/US2016/012305, dated Aug. 3, 2016, 18 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardia-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./Oct. 1996, 42(5):M381-M385.

(56) References Cited

OTHER PUBLICATIONS

Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschlul?. des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Rosch, J. et al., "The Birth, Early Years and Future of Interventional Radiology," J Vase Intery Radiol., Jul. 2003, 4:841-853.
Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
"Shape Memory Alloys," Retrieved from the Internet: <http://webdocs.cs.ualberta.ca/.about.database/MEMS/sma.html>, Nov. 14, 2012, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Extended European Search Report including the Written Opinion for Application No. EP 17813855.8 dated Jan. 15 2020, 9 pages.
Search Report dated Aug. 21, 2017 (PCT/US2017/036949).

\* cited by examiner

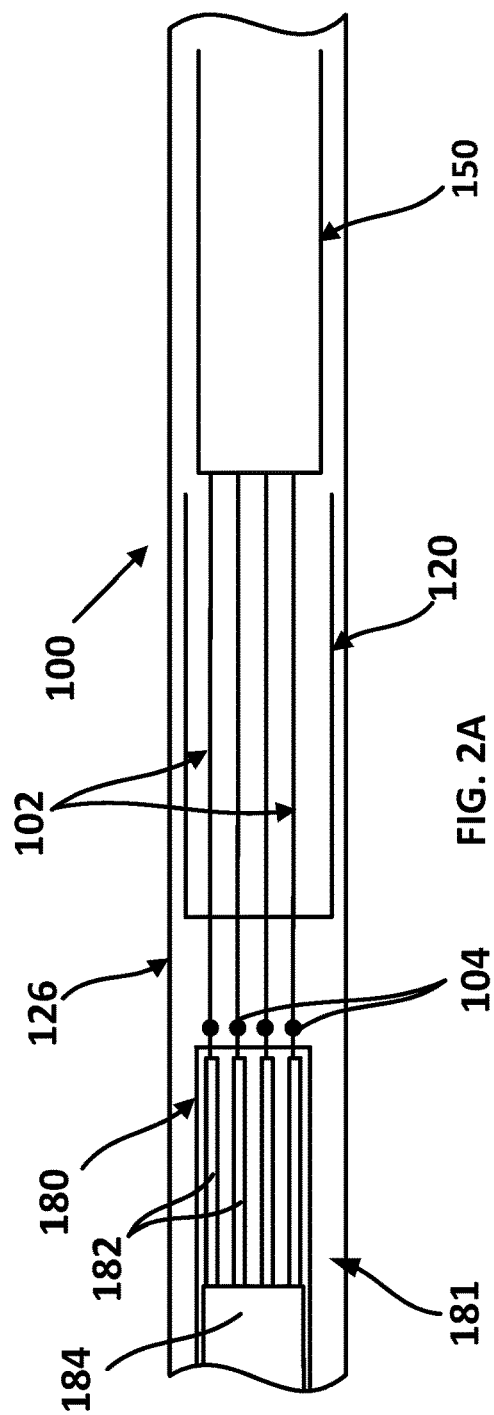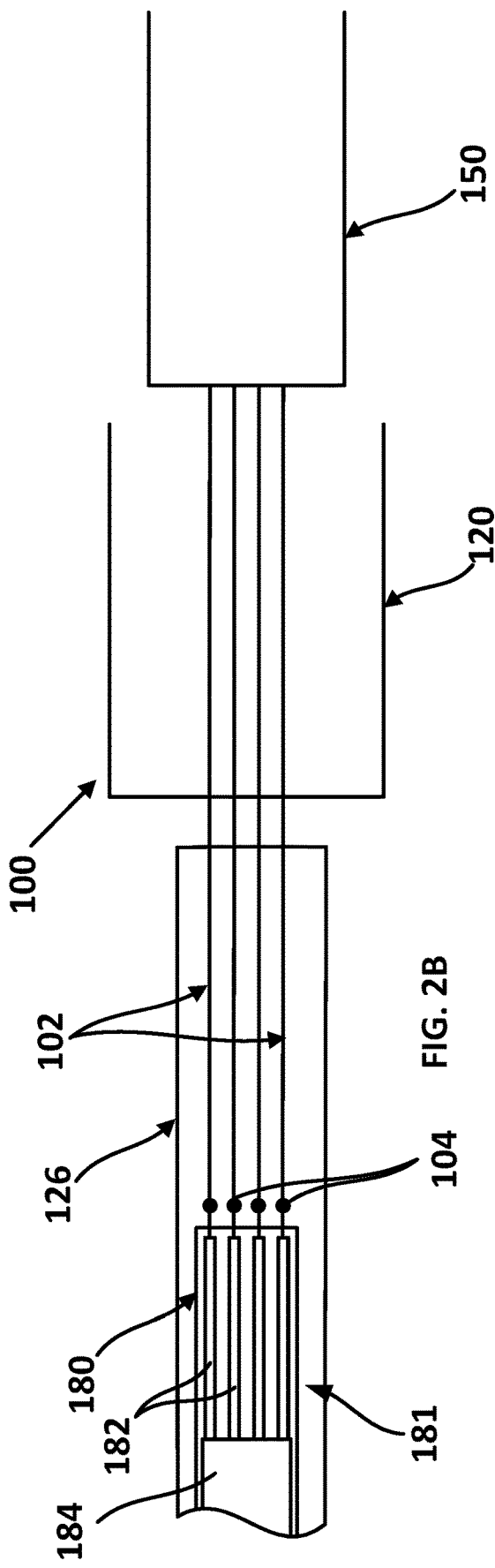

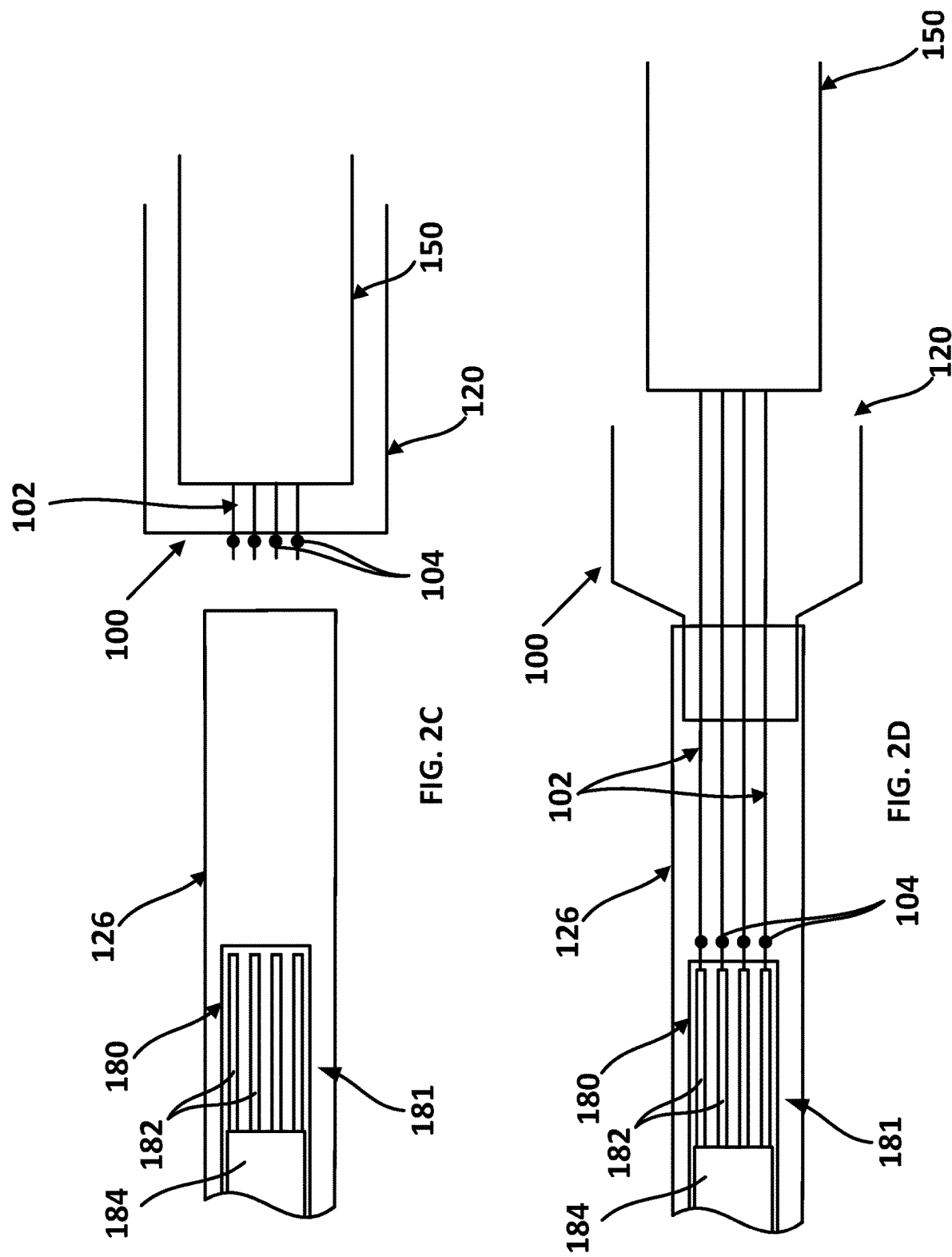

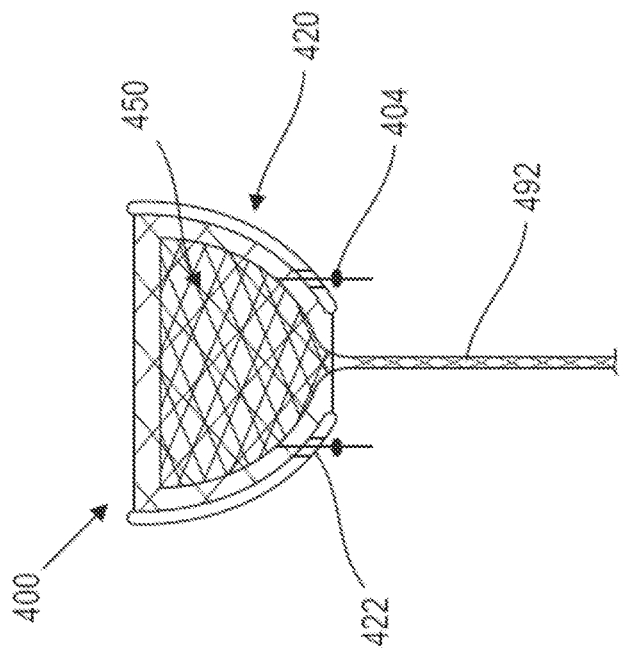
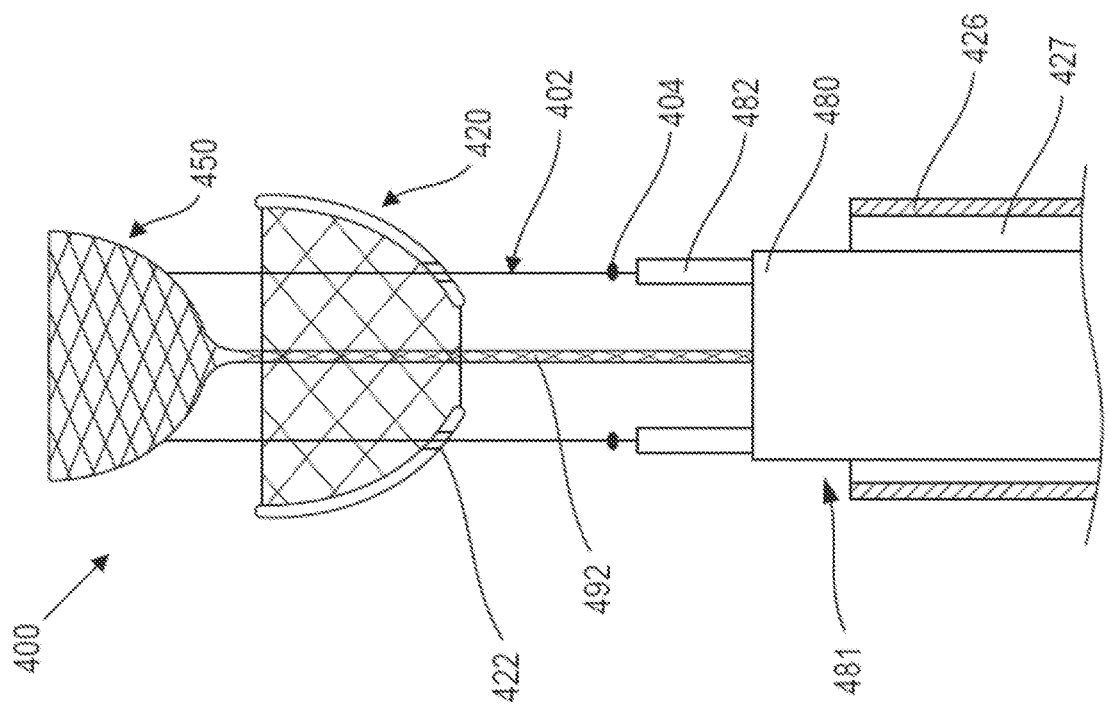

SEQUENTIAL DELIVERY OF TWO-PART PROSTHETIC MITRAL VALVE

CROSS-REFERENCE TO RELATED APPLICATIONS

This application is a national phase entry under 35 U.S.C. § 371 of International Application No. PCT/US2017/036949 filed Jun. 12, 2017, published in English, which claims priority to and the benefit of U.S. Provisional Patent Application No. 62/349,418, entitled "Sequential Delivery of Two-Part Prosthetic Mitral Valve," filed Jun. 13, 2016, the disclosures of which are all incorporated herein by reference in their entireties.

This application is also related to International Application No. PCT/US2016/012305, entitled "Prosthetic Mitral Valves and Apparatus and Methods for Delivery of Same," filed Jan. 6, 2016, which claims priority to and the benefit of International Application No. PCT/US2015/014572, entitled "Apparatus and Methods for Transfemoral Delivery of Prosthetic Mitral Valve," filed Feb. 5, 2015, which claims priority to and the benefit of U.S. Provisional Patent Application Ser. No. 61/935,899, entitled "Transfemoral Delivery of Prosthetic Mitral Valve," filed Feb. 5, 2014, and U.S. Provisional Patent Application No. 62/100,548, entitled "Apparatus and Methods for Transfemoral Delivery of Prosthetic Mitral Valve," filed Jan. 7, 2015, each of the disclosures of which is incorporated herein by reference in its entirety.

International Application No. PCT/US2016/012305 also claims priority to and the benefit of U.S. Provisional Patent Application No. 62/100,548, entitled "Apparatus and Methods for Transfemoral Delivery of Prosthetic Mitral Valve," filed Jan. 7, 2015, U.S. Provisional Patent Application Ser. No. 62/187,896, entitled "Apparatus and Methods for Delivery of a Prosthetic Mitral Valve," filed Jul. 2, 2015, and U.S. Provisional Patent Application Ser. No. 62/137,384, entitled "Apparatus and Method for Delivery of a Prosthetic Mitral Valve," filed Mar. 24, 2015. The disclosure of each of the foregoing applications is incorporated herein by reference in its entirety.

BACKGROUND

Embodiments are described herein that relate to devices and methods for use in the delivery and deployment of prosthetic valves.

Prosthetic heart valves can pose particular challenges for delivery and deployment within a heart. Valvular heart disease, and specifically, aortic and mitral valve disease, is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

Some known delivery methods include delivering a prosthetic mitral valve through an apical puncture site. In some such procedures, the valve is placed in a compressed configuration within a lumen of a delivery catheter of, for example, 34-36 Fr (i.e., an outer diameter of about 11-12 mm). Delivery of a prosthetic valve to the atrium of the heart can also be accomplished, for example, via a transfemoral approach, transatrially directly into the left atrium of the heart, or via a jugular approach. In such cases, it is desirable for the prosthetic valve to have a small outer perimeter or profile to allow insertion through a smaller delivery catheter of, for example, 28 Fr (i.e., an outer diameter of about 9 mm). Such a small outer perimeter or profile may also be desirable for delivery of a prosthetic heart valve via a transapical approach.

Thus, a need exists for prosthetic heart valves that can have a small profile during delivery while still maintaining the size and characteristics needed to perform their desired function within the heart.

A need also exists for devices and methods for delivering and deploying a prosthetic heart valve within a heart, with the valve disposed within a small diameter delivery sheath and then moving the valve to an expanded configuration within the heart.

SUMMARY

In some embodiments, an apparatus includes a prosthetic heart valve that includes an inner frame and an outer frame coupleable to the inner frame via sutures. The prosthetic heart valve is movable between a first configuration for delivery and a second configuration when implanted in a heart. The inner frame and the outer frame can be moved between a first position relative to each other in which the outer frame is disposed substantially axially proximal of the inner frame and a second position relative to each other in which the inner frame is nested substantially within the outer frame. The prosthetic heart valve is in the first configuration when the inner frame and the outer frame are in the first position and in the second configuration when the inner frame and the outer frame are in the second position.

BRIEF DESCRIPTION OF THE FIGURES

FIGS. 2A-2C are schematic illustrations of the portion of the prosthetic heart valve of FIGS. 1A and 1B, shown in a first, second, and third stage of deployment from a delivery system, respectively.

FIG. 2D is a schematic illustration of a portion of the prosthetic heart valve of FIGS. 1A and 1B, shown in an alternative stage of deployment from a delivery system.

FIG. 16A is a schematic illustration of a delivery device shown partially in cross-section, according to an embodiment, and a prosthetic heart valve, shown in a first configuration.

FIG. 16B is a schematic illustration of the prosthetic heart valve of FIG. 16A shown in a second configuration.

DETAILED DESCRIPTION

Figure 1A:
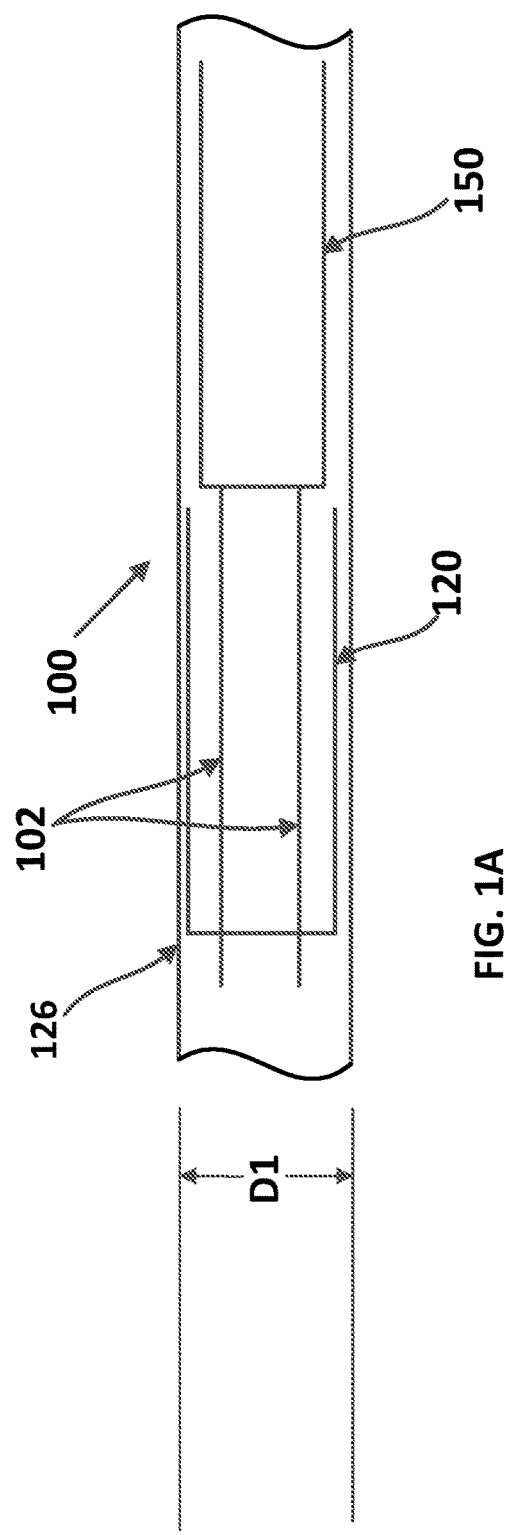
FIGS. 1A and 1B are schematic illustrations of a portion of a prosthetic heart valve, according to an embodiment, shown within a delivery sheath in a first configuration and a second configuration, respectively.

Apparatus and methods are described herein for prosthetic heart valves, such as prosthetic mitral valves, that can be configured to be moved to an axially extended configuration for sequential delivery of two portions of the prosthetic valve to within a heart of a patient. As described herein, in some embodiments, a prosthetic valve includes an outer frame and an inner frame. The prosthetic valve can be disposed within a delivery sheath in a compressed or collapsed configuration and such that the outer frame is axially separated from the inner frame. The prosthetic mitral valve can be formed with, for example, a shape-memory material. During deployment within a heart, the outer frame and the inner frame can be brought together into a substantially nested configuration and coupled to maintain the nested configuration. In some embodiments, slip knots can be used to secure the inner frame to the outer frame.

The delivery sheath can be used to deliver the prosthetic valve to within a patient's heart using a variety of different delivery approaches for delivering a prosthetic heart valve (e.g., a prosthetic mitral valve) where the prosthetic valve would enter the heart through the atrium of the heart. For example, the prosthetic valves described herein can be delivered transapically if desired, such as described in International Application No. PCT/US16/27770 (the '770 PCT application). In another example, the prosthetic valves described herein can be delivered using a transfemoral delivery approach as described in International Application No. PCT/US16/12305 (the '305 PCT application) incorporated by reference above or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 ("the '704 provisional application"), which is incorporated herein by reference in its entirety. In another example, a valve as described herein can be delivered via a transjugular approach, via the right atrium and through the atrial septum and into the left atrium as described in U.S. Provisional Patent Application Ser. No. 62/305,678, entitled "Apparatus and Methods for Delivery of Prosthetic Mitral Valve," filed Mar. 9, 2016 ("the '678 provisional application"), which is incorporated herein by reference in its entirety. After the delivery sheath has been disposed within the left atrium of the heart, the prosthetic mitral valve can be moved distally out of the delivery sheath such that the inner frame is first delivered from the delivery sheath and the outer frame is delivered subsequently. The inner frame can then be positioned relative to the outer frame such that the inner frame is nested within the outer frame. The prosthetic mitral valve can then be positioned within a mitral annulus of the heart.

In some embodiments, an apparatus includes a prosthetic heart valve that includes an inner frame and an outer frame coupled to the inner frame via sutures. The prosthetic valve is movable between a first configuration and a second configuration when implanted in a heart. The inner frame and the outer frame can be moved between a first position relative to each other in which the outer frame is disposed substantially axially proximal of the inner frame and a second position relative to each other in which the inner frame is substantially nested within the outer frame. In some embodiments, the outer frame can be disposed at a non-zero distance from the inner frame when in the first configuration. Sutures including slip knots coupled thereto can be used to secure the inner frame to the outer frame in the nested configuration. The prosthetic valve is in the first configuration when the inner frame and the outer frame are in the first position and in the second configuration when the inner frame and the outer frame are in the second position.

In some embodiments, a delivery system includes an outer delivery sheath that defines a lumen and a delivery device movably disposable within the lumen of the delivery sheath. The delivery device includes an inner sheath movably disposable within the lumen of the delivery sheath and defining a lumen, and at least one suture tube coupled to a tube positioning member that is movably disposed within the lumen of the inner sheath. Each of the suture tubes can receive therein a suture coupled to a prosthetic heart valve where the suture includes a sliding or slip knot. The suture tubes can be used to push the sliding knots to secure an inner frame of the prosthetic heart valve to an outer frame of the prosthetic heart valve, as described in more detail below. The delivery system can be used to deliver and deploy the prosthetic heart valve into a heart. The prosthetic heart valve can be placed in the lumen of the outer frame such that the inner frame and outer frame are collapsed or compressed. The outer frame and the inner frame are movable relative to each other between a first configuration in which the outer frame is disposed substantially axially proximal of the inner frame and a second configuration in which the inner frame is substantially nested within the outer frame. The prosthetic heart valve is disposed within the lumen of the delivery sheath with the outer frame and the inner frame in the first configuration.

In some embodiments, a method to deliver and deploy the heart valve using the delivery system described above includes inserting a distal end portion of the delivery sheath into a left atrium of a heart. The prosthetic mitral valve can be moved distally out of the delivery sheath causing the prosthetic mitral valve to at least partially assume a biased expanded configuration. The inner frame and/or the outer frame can then be moved relative to the other to transition the inner frame and the outer frame into the second configuration. For example, in some embodiments, the inner frame and the outer frame are loosely coupled together in the first configuration with sutures that include sliding knots or slip knots. To move the inner frame and outer frame to the second configuration, the sliding knots can be moved distally out of the delivery sheath along the sutures using the suture tubes while also pulling the sutures proximally relative to the sliding knots such that the inner frame is pulled proximally into the second position. The sliding knots can be used to secure the inner frame to the outer frame in the second configuration. The prosthetic mitral valve can then be positioned within a mitral annulus of the heart in a desired orientation.

Figure 1B:
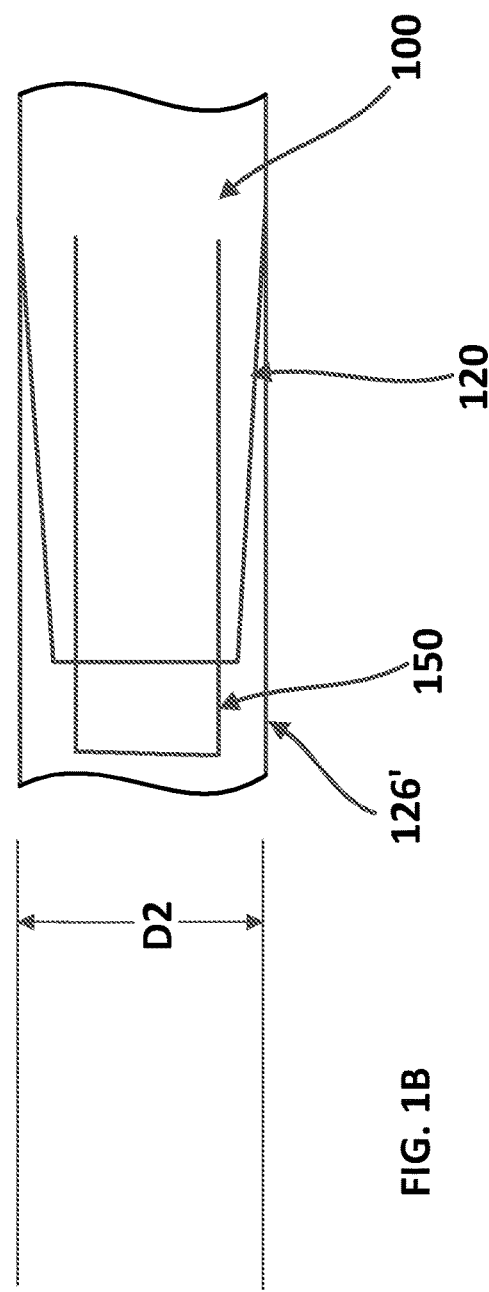

FIGS. 1A and 1B are schematic illustrations of a portion of a prosthetic heart valve 100, according to an embodiment, shown disposed within a lumen of a delivery sheath 126 and within a delivery sheath 126', respectively. FIGS. 2A-2D are schematic illustrations of a portion of a delivery system with the prosthetic heart valve 100 of FIGS. 1A and 1B shown in different stages of deployment from the delivery system. The prosthetic heart valve 100 (also referred to herein as "prosthetic valve" or "valve") can be, for example, a prosthetic mitral valve. The valve 100 includes an outer frame 120 and an inner frame 150. The outer frame 120 and the inner frame 150 can each be formed as a tubular structure and in the same or similar manner as described in more detail below for prosthetic valve 200 with reference to FIGS. 3-14. The outer frame 120 and the inner frame 150 can be coupled together via sutures 102 as described in more detail below. Additionally, in some embodiments, the outer frame 120 can include pre-formed atrial pockets. The valve 100 can also include other features, such as those described with respect to FIGS. 3-14 below. For illustration purposes, only the inner frame 150 and the outer frame 120 are discussed with respect to FIGS. 1A-2D.

The outer frame 120 is configured to have a biased expanded or undeformed shape and can be manipulated and/or deformed (e.g., compressed or constrained) and, when released, return to its original (expanded or undeformed) shape. For example, the outer frame 120 can be formed of materials, such as metals or plastics, having shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 150 can be formed from a laser-cut tube of Nitinol®. The inner frame 150 can also have a biased expanded or undeformed shape and can be manipulated and/or deformed (e.g., compressed and/or constrained) and, when released, return to its original (expanded or undeformed) shape. Further details regarding the inner frame 150 and the outer frame 120 are described below with respect to valve 200 and FIGS. 3-14.

The valve 100 can be delivered and deployed within a heart (e.g., left atrium) using a variety of different delivery approaches including, for example, a transfemoral delivery approach, as described in the '305 PCT application, a transatrial approach, as described in the '704 provisional application, a transapical approach, as described in the '770 PCT application, or a transjugular approach, as described in the '678 provisional application. As described above, in some situations, it may be desirable to use a smaller delivery sheath and, when delivering a prosthetic valve to the heart, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

More specifically, the valve 100 can have a biased expanded configuration (as shown in FIGS. 2B and 2C) and a compressed or collapsed configuration (as shown in FIGS. 1A, 1B, and 2A). The expanded configuration allows the valve 100 to function when implanted within the heart. The valve 100 can be moved to the compressed or collapsed configuration for delivery of the valve 100 to the heart of a patient.

As shown in FIG. 1A, the valve 100 can be delivered to the heart of a patient within a delivery sheath 126 in an axially extended configuration. More specifically, the inner frame 150 can be disposed within the delivery sheath 126 substantially distally of the outer frame 120. In some embodiments, the inner frame 150 can be disposed entirely distally of a distal end of the outer frame 120. In other words, the inner frame 150 is disposed at a non-zero distance from the outer frame 120. In other embodiments, the inner frame 150 can be disposed within the delivery sheath 126 such that the proximal end of the inner frame 150 is in abutting contact with the distal end of the outer frame 120. In other embodiments, the inner frame 150 can be disposed such that a portion of the inner frame 150 is within the outer frame 120, but the inner frame 150 is not within the outer frame 120 to the same extent as when the inner frame 150 is nested within the outer frame 120 when the valve 100 is fully assembled. The inner frame 150 can be coupled to the outer frame 120 via sutures 102. When the valve 100 is in the extended configuration, the sutures 102 extend from the inner frame 150 to the outer frame 120 and then proximally from the outer frame 120 into a delivery device 181 (see FIGS. 2A-2D), as described in more detail below.

With the valve 100 in the axially extended configuration, the valve 100 can be placed within a lumen of the delivery sheath 126 (as shown in FIG. 1A) for delivery of the valve 100 to the left atrium of the heart. When placed within the lumen of the delivery sheath 126, the valve 100 can be moved to a collapsed or compressed configuration in which the outer diameter or outer perimeter of the valve 100 is reduced. Said another way, the outer frame 120 and the inner frame 150 can each be moved to a collapsed or compressed configuration in which the outer diameter of each of the outer frame 120 and the inner frame 150 are reduced. Because the valve 100 is in the axially extended configuration, the valve 100 is able to be placed within a smaller delivery sheath 126 than would otherwise be possible. For example, for comparison purposes, FIG. 1B illustrates the valve 100 placed within a lumen of a delivery sheath 126' where the outer frame 120 and the inner frame 150 of the valve 100 are disposed in a nested configuration rather than an axially extended configuration within the delivery sheath 126'. As shown in FIG. 1B, an outer diameter of the valve 100 is reduced compared to the valve 100 in an uncompressed configuration (such as is shown in FIGS. 2B and 2C), but not to as small of a diameter as for the valve 100 when placed in a delivery sheath 126 when in the axially extended configuration (shown in FIG. 1A). Thus, in FIG. 1A, the valve 100 has an overall outer perimeter or outer diameter D1 and in FIG. 1B, the valve 100 has an overall outer perimeter or outer diameter D2, which is greater than D1.

Thus, by disposing the outer frame 120 and the inner frame 150 in the axially extended configuration, the valve 100 can be collapsed into a smaller overall diameter, i.e. placed in a smaller diameter delivery sheath 126, than would be possible if the outer frame 120 and the inner frame 150 of the valve 100 were merely nested and collapsed radially (as shown in FIG. 1B). This is because when the inner frame 150 is nested within an interior of the outer frame 120, the outer frame 120 must be collapsed around the inner frame 150. For example, in some embodiments, the inner frame 150 and the outer frame 150 are disposed concentrically when nested together. In the axially extended configuration, the inner frame 150 and the outer frame 120 are arranged axially with respect to each other (i.e., the inner frame is not nested or is only partially nested within the outer frame 150), such that the outer frame 120 can be collapsed without needing to accommodate all of the structure of the inner frame 150 inside it. In other words, with the inner frame 150 disposed mostly inside or nested within the outer frame 120, the layers or bulk of the frame structures cannot be compressed to as small a diameter. In addition, if the frames are nested, the structure is less flexible, and therefore, more force is needed to bend the valve, e.g. to pass through tortuous vasculature or to make tight turns in the left atrium after passing through the atrial septum to be properly oriented for insertion into the mitral valve annulus.

As noted above, FIGS. 2A-2C are schematic illustrations of a portion of a delivery system with the prosthetic heart valve 100 of FIGS. 1A and 1B shown in various stages of deployment. As shown in FIG. 2A, the valve 100 is disposed in the axially extended configuration within the delivery sheath 126. Said another way, when the valve 100 is disposed within the delivery sheath 126, the outer frame 120 and the inner frame 150 are in a collapsed or compressed configuration and axially extended or spaced relative to each other.

As shown in FIG. 2A, the outer frame 120 and the inner frame 150 are coupled via sutures 102. Although four sutures 102 are shown, any suitable number of sutures 102 can be used to couple the outer frame 120 to the inner frame 150. The sutures 102 can be securely attached to the inner frame 150 via any suitable method. Additionally, the outer frame 120 can include apertures (not shown) through which the sutures 102 can be movably disposed. Each of the sutures 102 includes and/or is coupled to a slip knot (also referred to herein as sliding knot) 104 which is movable along each suture 102. The sutures 102 and slip knots 104 can be used to move the valve 100 to the nested configuration as described in more detail below. In some embodiments, after the prosthetic valve has been deployed out of the delivery sheath 126, the sutures 102 can be pulled proximally such that the inner frame 150 is pulled proximally into the nested configuration. The slip knots 104 can then be translated along the sutures 102 toward the valve 100 such that the outer frame 120 is secured to the inner frame 150. For example, in some embodiments, the apertures in the outer frame 120 can be smaller in diameter than the diameter of the slip knots 104, such that the outer frame 120 cannot move proximally beyond the location of the slip knots 104. Additionally, in some embodiments, during deployment of the prosthetic valve 100, the distal end of the delivery sheath 126 can act as a stop (i.e., limit proximal movement of the valve 100). Said another way, as the sutures 102 are pulled proximally during deployment, the expanded or partially expanded valve 100 cannot be pulled proximally beyond the distal end of the delivery sheath 126 (i.e., into the delivery sheath 126).

As shown in FIGS. 2A-2C, the delivery device 181 can include an inner sheath 180 axially movable within the lumen of the delivery sheath 126. One or more suture tubes 182 can be disposed within and can be axially movable relative to the inner sheath 180. Each suture tube 182 can define a suture lumen within which a suture 102 can be movably disposed. Each suture tube 182 can be translated along a suture 102 and engage with a corresponding slip knot 104 such that the slip knot 104 is axially movable by the suture tube 182 relative to the suture 102. In some embodiments, each slip knot 104 is movable by the corresponding suture tube 182 because the inner diameter of each suture tube 182 (i.e., the diameter of each suture lumen) at the distal end of each suture tube 182 is less than the diameter of each corresponding slip knot 104. In other embodiments, each suture tube 182 can include an engagement feature (not shown) capable of engaging with each slip knot 104 for distal and/or proximal translation of each slip knot 104 along each corresponding suture 102. Although four suture tubes 182 are shown in FIGS. 2A-2C, any suitable number of suture tubes 182 can be used. For example, in some embodiments, the number of suture tubes 182 can be equal to the number of sutures 102. In other embodiments, the number of suture tubes 182 can be greater than or less than the number of sutures 102.

A tube positioning member 184 can be coupled to each of the suture tubes 182. In some embodiments, the tube positioning member 184 can be, for example, a sheath within which the suture tubes 182 are securely attached. In other embodiments, the tube positioning member 184 can be a frame securely coupled to each of the suture tubes 182. In other embodiments, the tube positioning member 184 can be a sheath within which a frame is secured such that the suture tubes 182 can be attached to the frame. Additionally, the tube positioning member 184 can define a central lumen (not shown) such that a tether (not shown) coupled to the valve 100 can be threaded through and movably disposed therethrough. The suture tubes 182 can be fixed to the tube positioning member 184 such that axial movement of the tube positioning member 184 relative to the inner sheath 180 causes simultaneous movement of the suture tubes 182. In alternative embodiments, the suture tubes 182 can each be controlled independently. Although the delivery device 181 is shown as including an inner sheath 180, in some embodiments, the delivery device 181 does not include an inner sheath 180.

FIG. 2B shows the valve 100 after the valve 100 has been moved out of the distal end of the delivery sheath 126 and into an expanded configuration. As shown in FIG. 2B in comparison to FIG. 2A, the inner frame 150 and the outer frame 120 have a larger diameter in the expanded configuration than in the compressed configuration within the delivery sheath 126. In some embodiments, the inner sheath 180 can engage with the valve 100 to control the position of the valve 100 relative to the delivery sheath 126 and control the sequential delivery of the inner frame 150 and the outer frame 120 from the delivery sheath 126. In such embodiments, the inner sheath 180 can push the outer frame 120 distally into abutting contact with the inner frame 150. Further distal movement of the inner sheath 180 can cause the outer frame 120 to push the inner frame 150 distally such that the inner frame 150 is pushed from the distal end of the delivery sheath 126. The inner sheath 180 can continue to push the outer frame 120 distally until the outer frame 120 is also pushed distally of the distal end of the delivery sheath 126. In other embodiments, another component (not shown) can be used similarly to push the valve 100 distally such that the inner frame 150 and the outer frame 120 are sequentially delivered from the delivery sheath 126. Alternatively, the inner sheath 180 or another component (not shown) can prevent proximal movement of the valve 100 while the delivery sheath 126 is retracted relative to the valve 100 such that the inner frame 150 and the outer frame 120 can sequentially transition into the expanded configuration. In the configuration of FIG. 2B, the inner frame 150 and the outer frame 120 are each in a biased expanded configuration and the inner frame 150 is still axially disposed relative to the outer frame 120.

FIG. 2C shows the inner frame 150 nested within the outer frame 120. As shown in FIG. 2C, the position of the inner frame 150 relative to the outer frame 120 is secured by the slip knots 104. The slip knots 104 can be moved to the position shown in FIG. 2C by the suture tubes 182. As described above, the sutures 102 can be pulled proximally through the suture tubes 182 while the slip knots 104 are held stationary by the distal end of the suture tubes 182 such that the inner frame 150 is moved proximally into a nested position within the outer frame 120. Although the slip knots 104 are described as being held stationary, in some embodiments, the slip knots 104 can be pushed distally by the suture tubes 182 while the sutures 102 are being pulled proximally through the suture tubes 182. After the inner frame 150 is nested within the outer frame 120, the suture tubes 182 can be distally translated along the sutures 102 such that each slip knot 104 is moved distally along the sutures 102 by the distal end of a suture tube 182. The suture tubes 182 can be extended from the distal end of the delivery sheath 126 such that the slip knots 104 are pushed into contact with the outer frame 120 and the inner frame 150 and the outer frame 120 are secured relative to each other. Although the suture tubes 182 are described as not being extended from the distal end of the delivery sheath 126 until after the valve 100 is in the nested configuration, in some embodiments the suture tubes 182 can be extended from the distal end of the delivery sheath 126 prior to pulling the sutures 102 proximally to pull the inner frame 150 into the nested position within the outer frame 120. In such embodiments, the slip knots 104 would be pushed along the sutures 102 by the suture tubes 182 to a position distal of the delivery tube 126 prior to the proximal movement of the inner frame 150 into the nested position within the outer frame 120. In some embodiments, the distal movement of the slip knots 104 via distal movement of the suture tubes 182 can occur simultaneously while the sutures 102 are pulled proximally. When the inner frame 150 and the outer frame 120 are properly positioned relative to each other and secured by the slip knots 104, the sutures 102 can be severed proximally of the location of the slip knots 104 and the portion proximal of the severance can be removed. In some embodiments, the suture tubes 182 can each include a cutting feature (not shown) for separation and removal of a portion of each suture 102 proximal of each slip knot 104. In some embodiments, after the inner frame 150 and the outer frame 120 are secured to each other, a tether (not shown) attached to the valve 100 can be used to position the valve 100 in the native annulus. For example, a tether can be coupled to the inner frame 150 prior to delivery of the valve 100 to the left atrium. Once the valve 100 is positioned in the left atrium, the tether can be pulled such that the valve 100 is seated in the native annulus.

FIG. 2D is a schematic illustration of a stage of an alternative method of delivering the valve 100 from the delivery sheath 126. The inner frame 150 can be delivered from the distal end of the delivery sheath 126 similarly as described above with reference to FIG. 2B. For example, the inner sheath 180 can engage with the valve 100 to control the sequential delivery of the inner frame 150 and the outer frame 120 from the delivery sheath 126. The inner sheath 180 can push the outer frame 120 distally into abutting contact with the inner frame 150. Further distal movement of the inner sheath 180 can cause the outer frame 120 to push the inner frame 150 distally such that the inner frame 150 is pushed from the distal end of the delivery sheath 126. The inner sheath 180 can continue to push the outer frame 120 distally such that the outer frame 120 begins to transition to the expanded configuration as it is partially deployed from the distal end of the delivery sheath 126, as shown in FIG. 2D. In other embodiments, another component (not shown) can be used similarly to push the valve 100 distally such that the inner frame 150 is delivered and the outer frame 120 is partially delivered from the delivery sheath 126. Alternatively, the inner sheath 180 or another component (not shown) can prevent proximal movement of the valve 100 while the delivery sheath 126 is retracted relative to the valve 100 such that the inner frame 150 is delivered and transitions into the expanded configuration and the outer frame 120 is partially delivered and partially transitions into the expanded configuration. In the configuration of FIG. 2D, the inner frame 150 is in a biased expanded configuration, the outer frame is in a partially expanded configuration, and the inner frame 150 is still axially disposed relative to the outer frame 120.

With the outer frame 120 in the partially deployed position, the sutures 102 can be pulled proximally through the suture tubes 182 while the outer frame 120 is held stationary at the distal end of the delivery sheath 126 such that the inner frame 150 is moved proximally into a partially nested position within the outer frame 120. After the inner frame 150 is partially nested within the outer frame 120 and when the outer frame 120 is in the partially deployed position, the slip knots 104 can be pushed distally along at least a portion of the sutures 104 by the suture tubes 182. The outer frame 120 can then be pushed distally into the fully expanded, fully deployed configuration. For example, in some embodiments, the inner sheath 180 can continue to push the outer frame 120 distally until the outer frame 120 is pushed distally of the distal end of the delivery sheath 126. While the outer frame 120 is being pushed distally from the delivery sheath 126 and/or after the outer frame 120 has been moved to the expanded configuration, the sutures 102 can be pulled further proximally such that the inner frame 150 is moved to a fully nested position within the outer frame 120. The slip knots 104 can be moved to the position shown in FIG. 2C by the suture tubes 182 such that the position of the inner frame 150 relative to the outer frame 120 is secured by the slip knots 104, as described above with reference to FIG. 2C.

The valve 100 described above can be constructed the same as or similar to the valve 200 described with respect to FIGS. 3-14. For example the inner frame 150 and the outer frame 120 described above can include the same as or similar features as described for the valve 200. Although valve 200 is described as being coupled in a nested configuration prior to being delivered to the heart, the inner frame assembly and the outer frame assembly of the valve 200 can alternatively be delivered in a sequential manner as described above for the valve 100.

Figure 3:
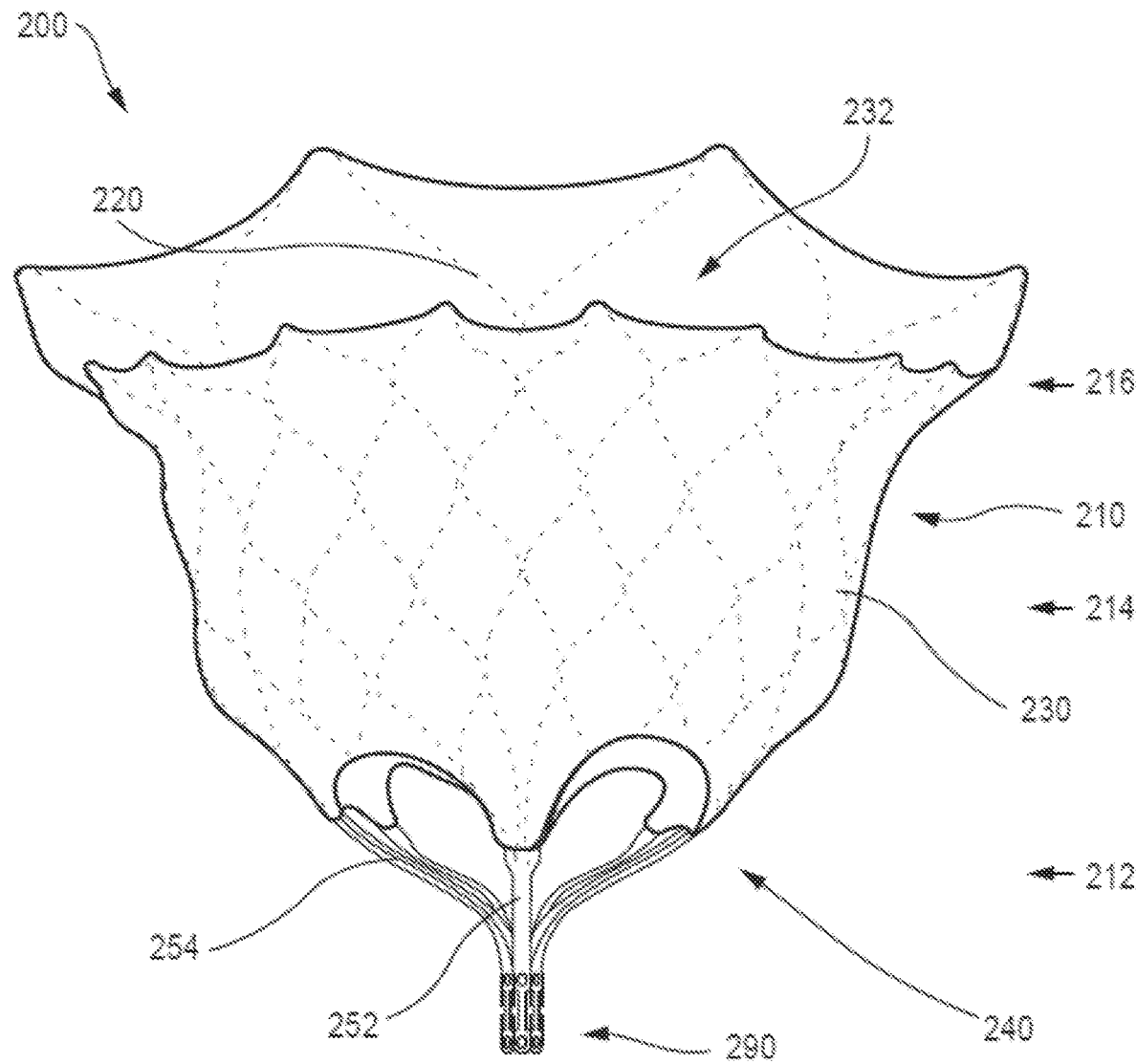
FIGS. 3-5 are front, bottom, and top views of a prosthetic heart valve according to an embodiment.
Figure 4:
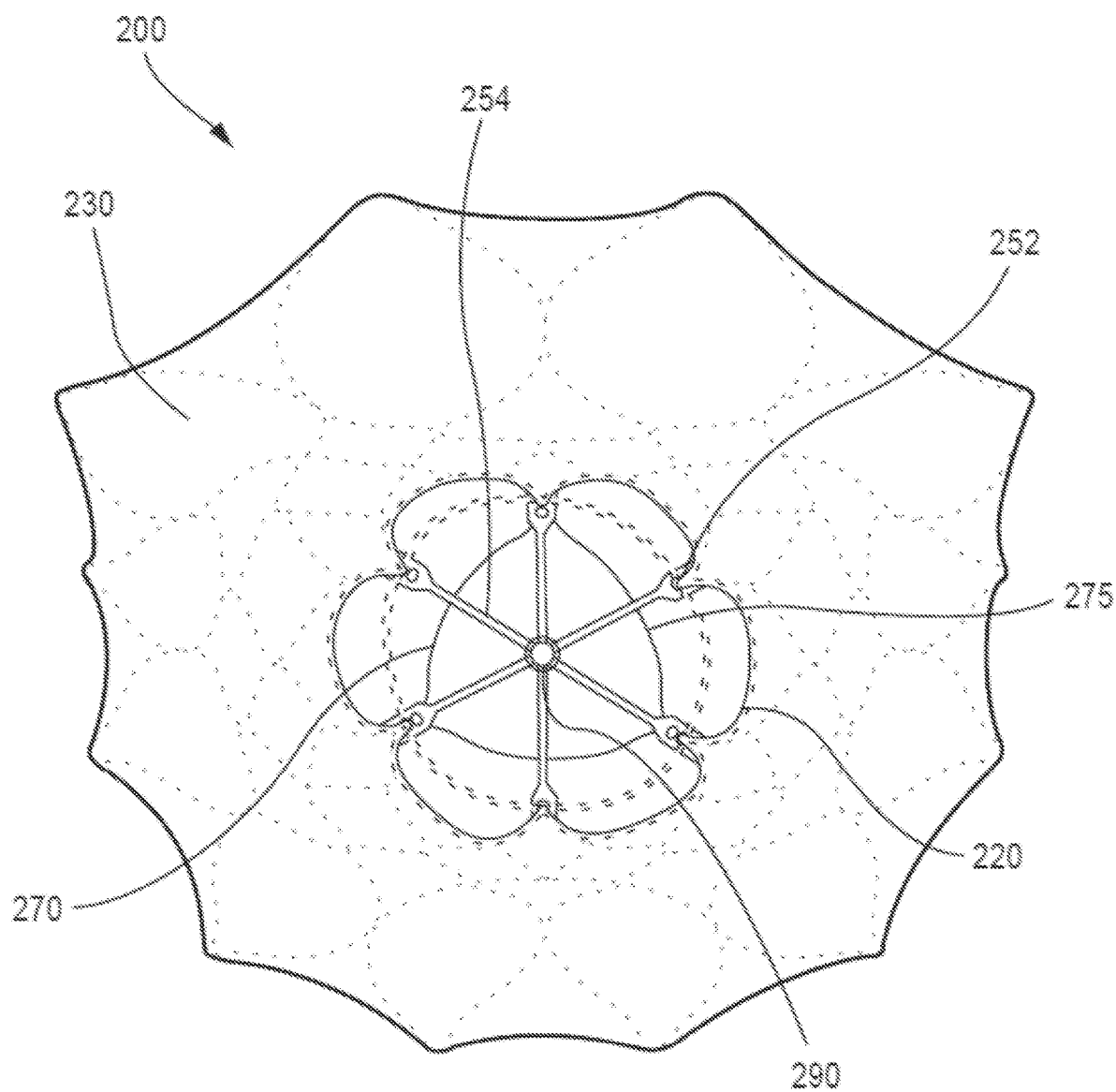
Figure 5:
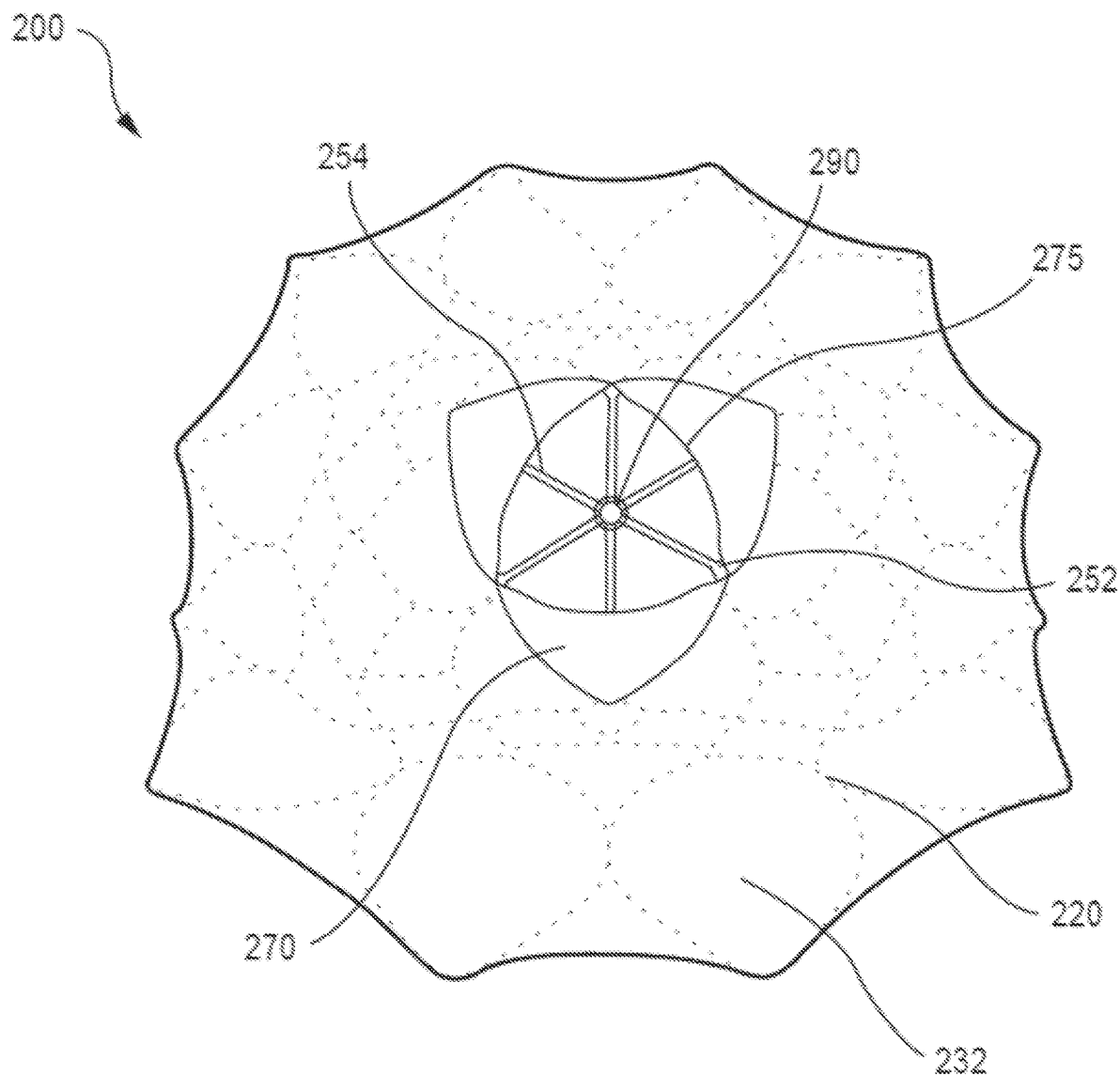

The prosthetic heart valve 200 can be delivered and deployed within a left atrium of a heart using a variety of different delivery approaches including, for example, a transfemoral delivery approach, a transatrial delivery approach, a transapical delivery approach, a transjugular delivery approach, etc. FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, as a support to carry inner valve assembly 240, and/or as a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 have a D-shaped cross-section. In this manner, the outer frame assembly 210 promotes a suitable fit into the annulus of the native atrioventricular valve.

Inner valve assembly 240 includes an inner frame 250 (see, e.g., FIGS. 6-8 and 12-14), an outer covering (not shown), and leaflets 270 (see, e.g., FIGS. 4 and 5). As shown, for example, in FIG. 7, the inner valve assembly 240 includes an upper portion having a periphery formed with multiple arches. The inner frame 250 includes six axial posts or frame members that support the outer covering and leaflets 270. Leaflets 270 are attached along three of the posts, shown as commissure posts 252 (best illustrated in FIG. 4), and the outer covering (not shown) is attached to the other three posts, 254 (best illustrated in FIG. 4), and optionally to commissure posts 252. Each of the outer covering and leaflets 270 are formed of approximately rectangular sheets of material, which are joined together at their upper, or atrium end. The lower, ventricle end of the outer covering may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering (not shown) of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 6:
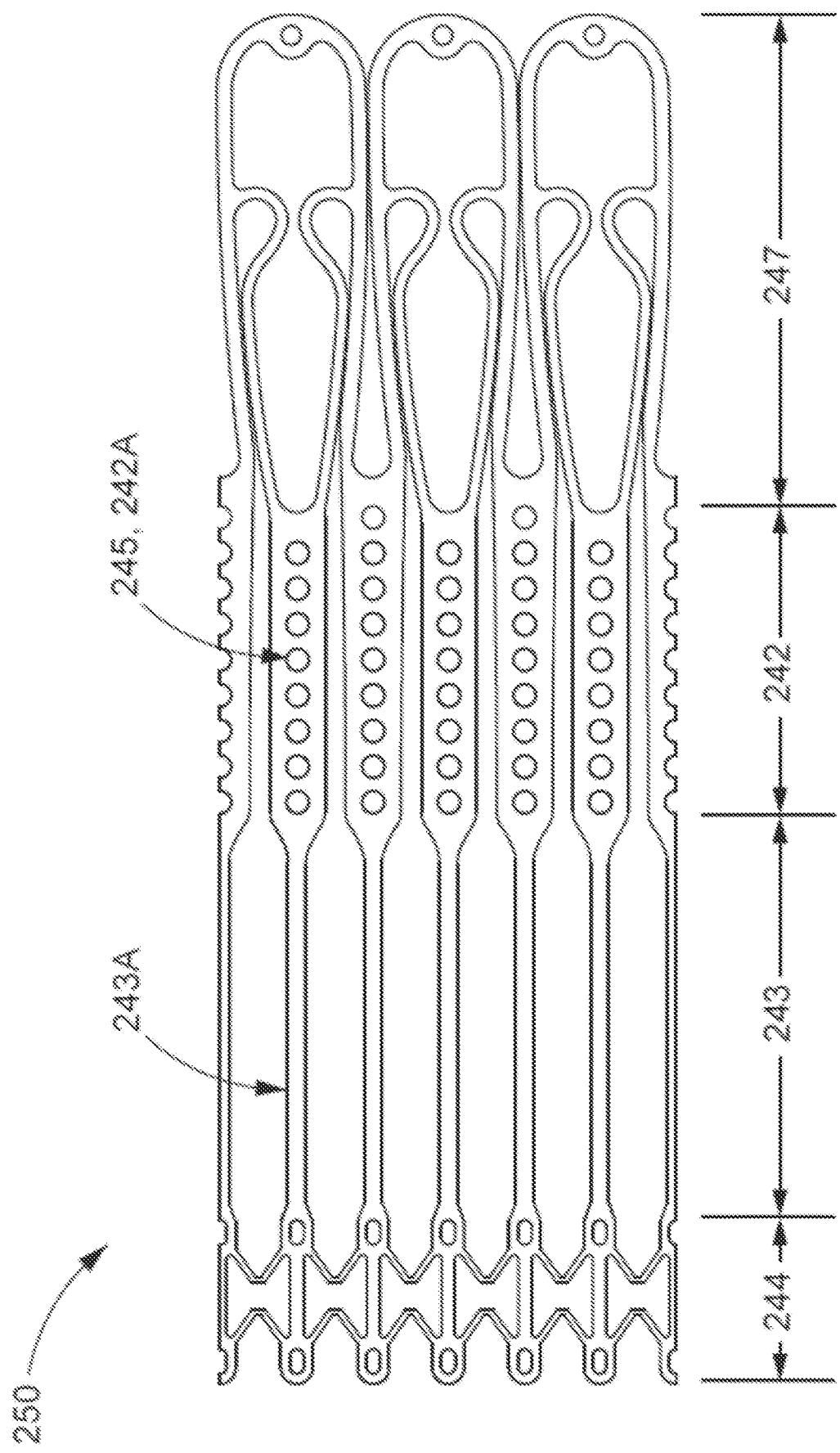
FIG. 6 is an opened and flattened view of the inner frame of the prosthetic heart valve of FIGS. 3-5, in an unexpanded configuration.
Figure 7:
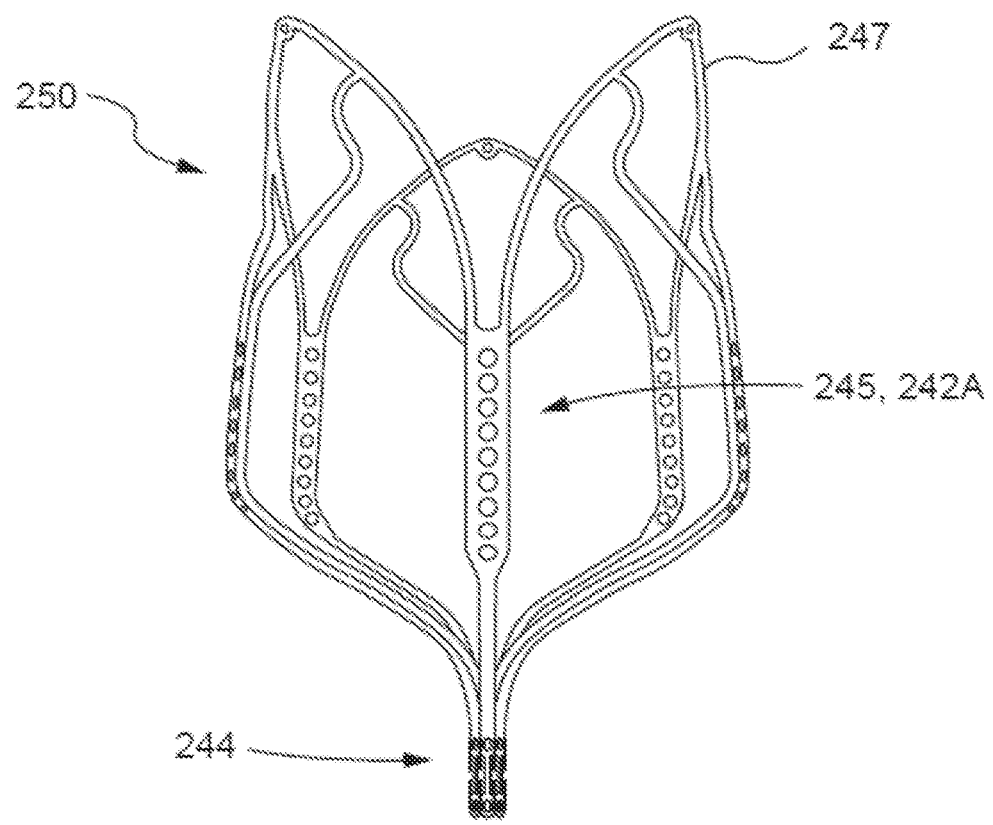
FIGS. 7 and 8 are side and bottom views, respectively, of the inner frame of FIG. 6 in an expanded configuration.
Figure 8:
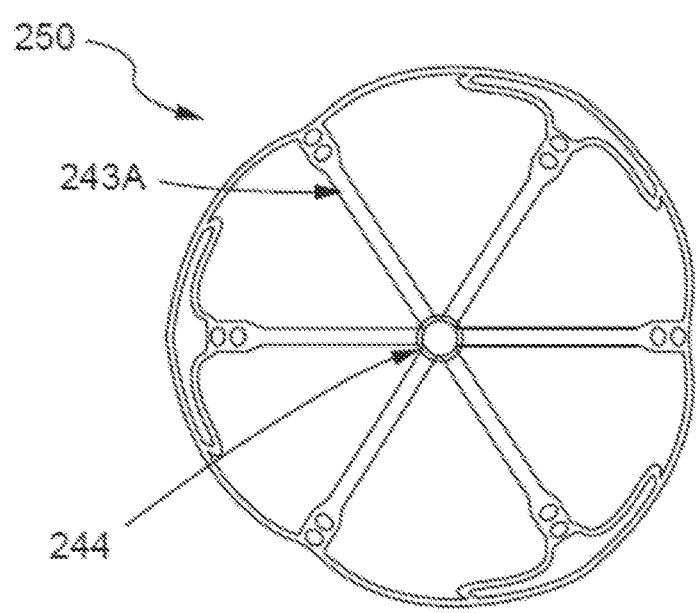

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of Nitinol®. Inner frame 250 is illustrated in FIG. 6 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 250, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed configuration (i.e., the final, deployed configuration) in side view and bottom view in FIGS. 7 and 8, respectively.

Figure 9:
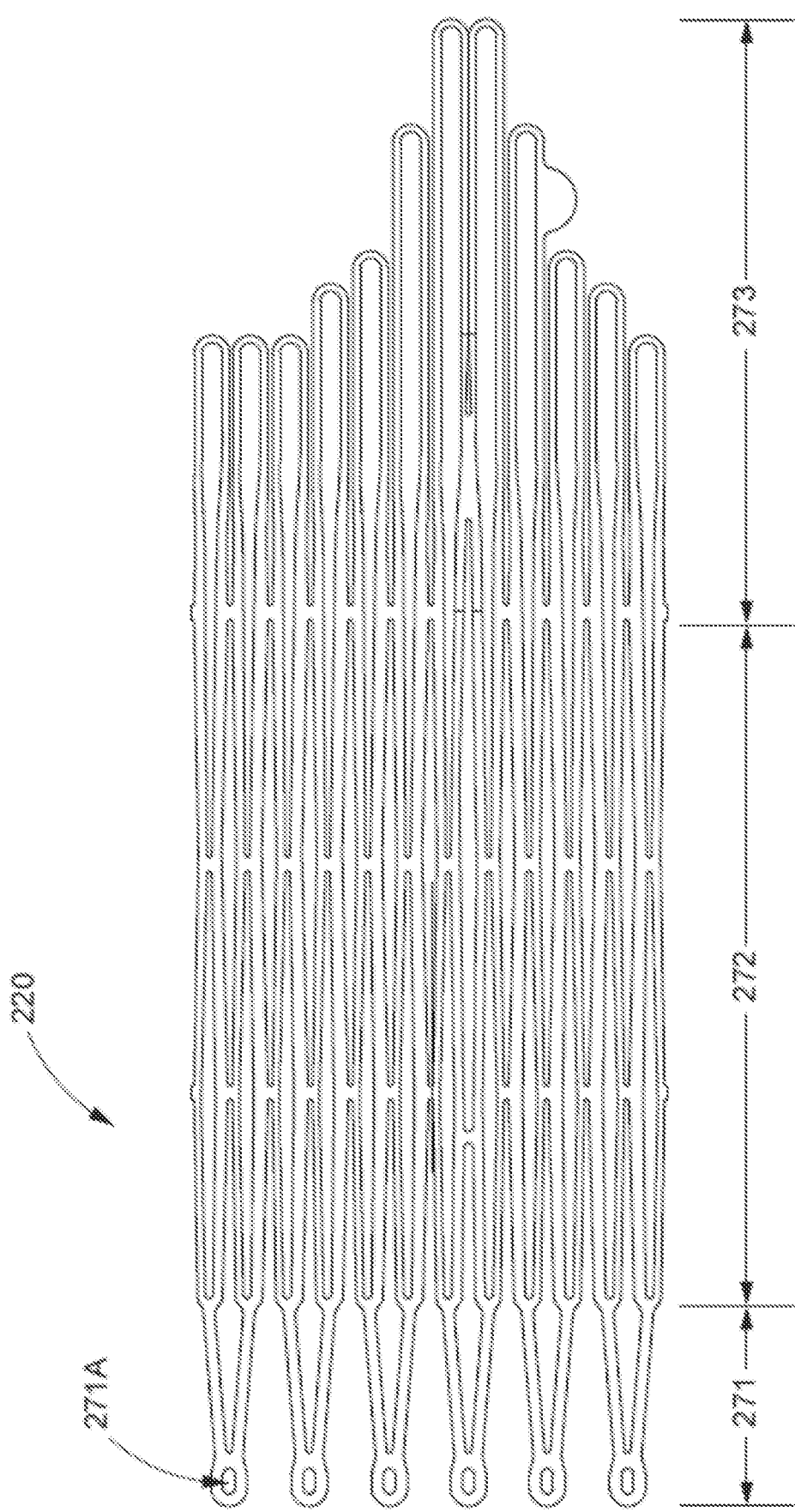
FIG. 9 is an opened and flattened view of the outer frame of the valve of FIGS. 3-5, in an unexpanded configuration.
Figure 10:
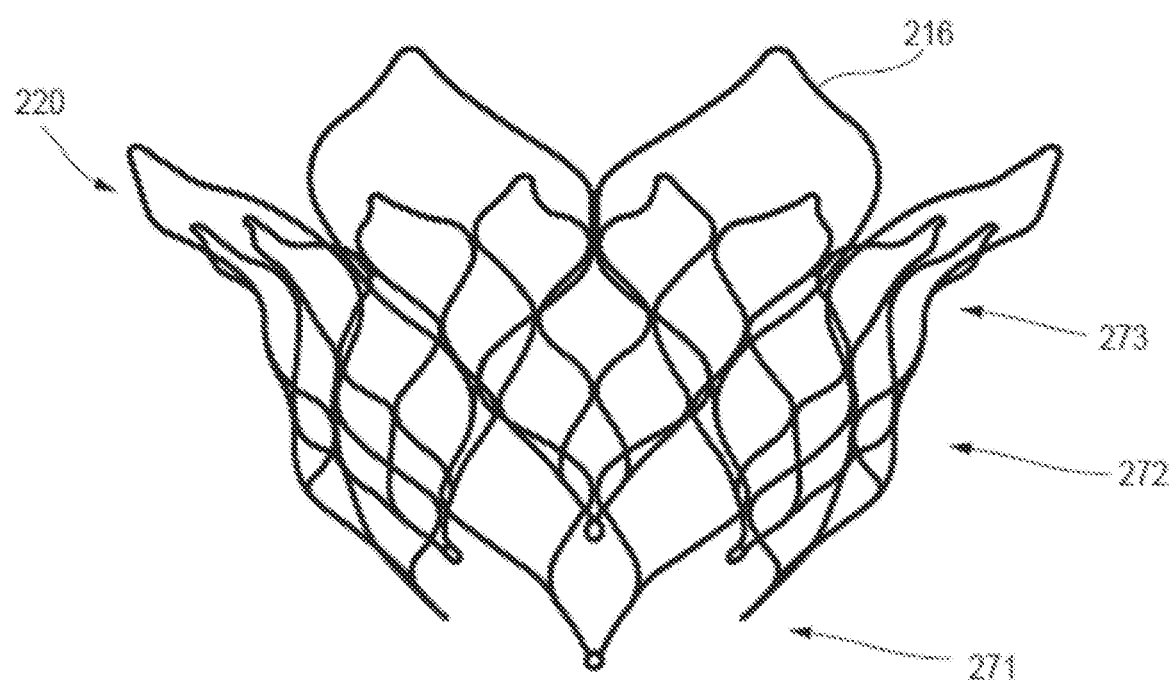
FIGS. 10 and 11 are side and top views, respectively, of the outer frame of FIG. 9 in an expanded configuration.
Figure 11:
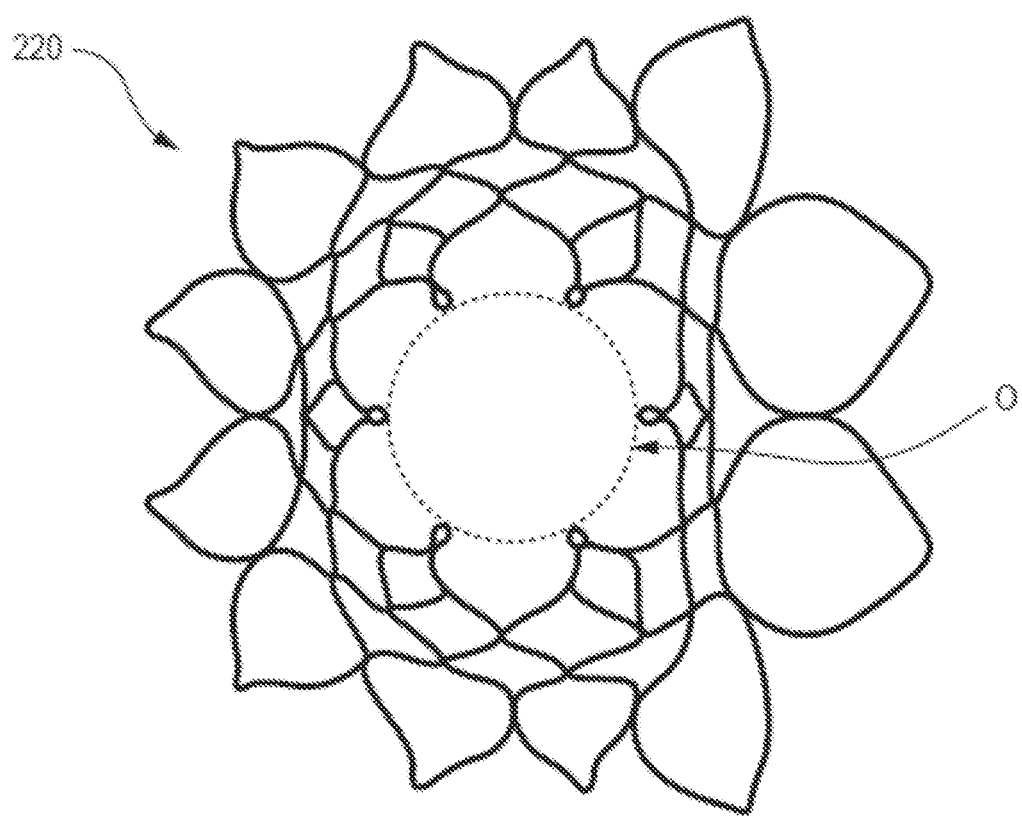

Outer frame 220 of valve 200 is shown in more detail in FIGS. 9-11. In this embodiment, outer frame 220 is also formed from a laser-cut tube of Nitinol®. Outer frame 220 is illustrated in FIG. 9 in an undeformed, initial state, e.g., as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed configuration (i.e. the final, deployed configuration) in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
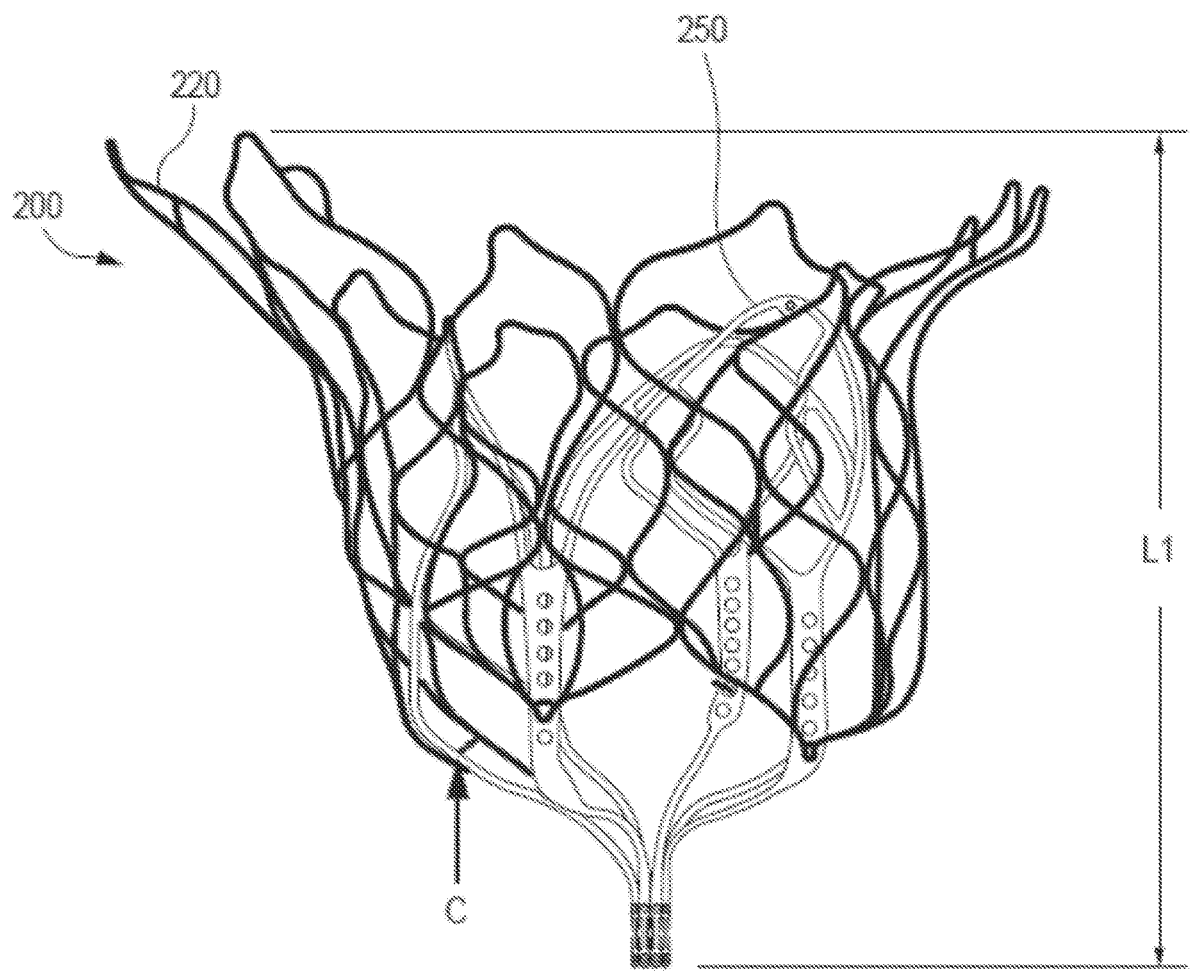
FIGS. 12-14 are side, front, and top views of an assembly of the inner frame of FIGS. 6-8 and the outer frame of FIGS. 9-11.
Figure 13:
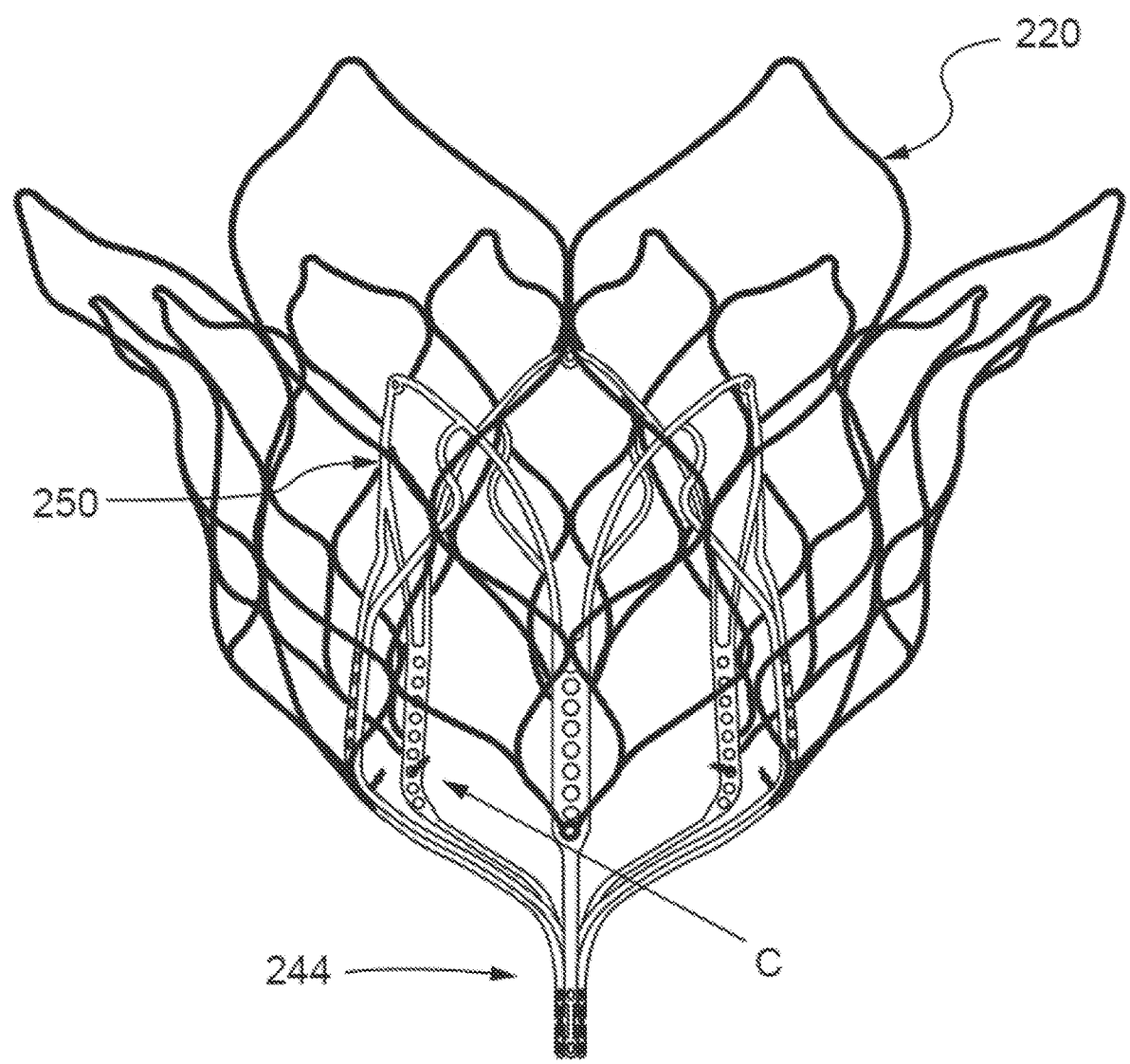
Figure 14:
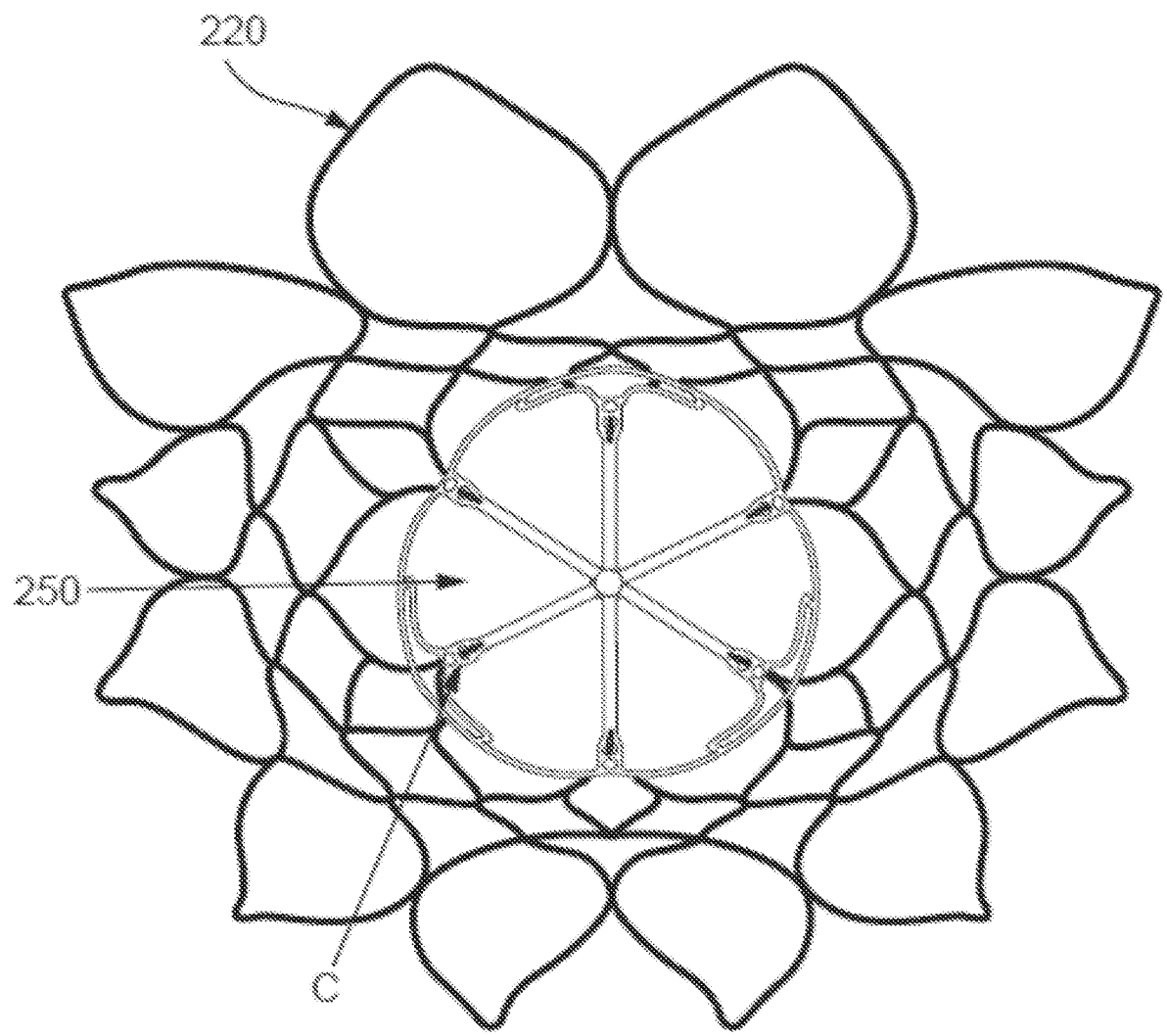

Outer frame 220 and inner frame 250 are shown coupled together in FIGS. 12-14, in front, side, and top views, respectively. The two frames (220, 250) collectively form a structural support for a prosthetic valve such as valve 200. The frames support the valve leaflet structure (e.g., leaflets 270) in the desired relationship to the native valve annulus, support the coverings (e.g., outer covering 230 and inner covering 232 of outer frame assembly 210, and the outer covering of the inner valve assembly) for the two frames (220, 250) to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall.

In this embodiment, the outer frame 220 and the inner frame 250 are connected at six coupling points (representative points are identified as "C"). The coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it. As described above, the outer frame 220 and inner frame 250 can alternatively be coupled with sutures and delivered in a sequential manner and secured with, for example, slip knots as described herein.

Figure 15B:
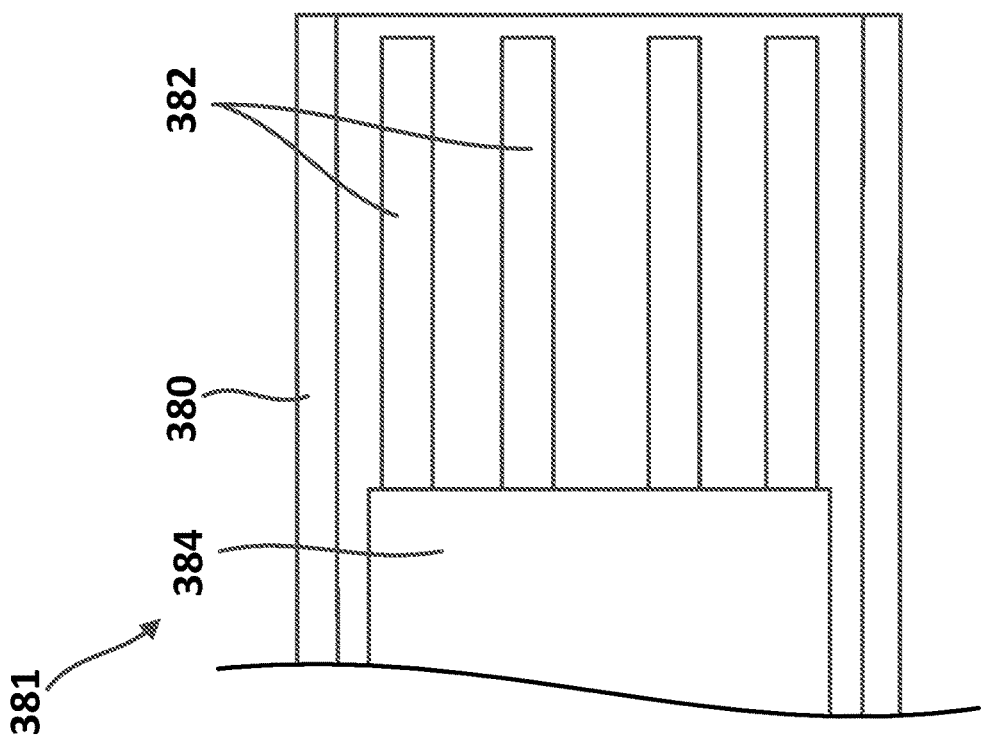
FIG. 15B is a schematic illustration of a side view of a portion of the delivery device of FIG. 15A.
Figure 15A:
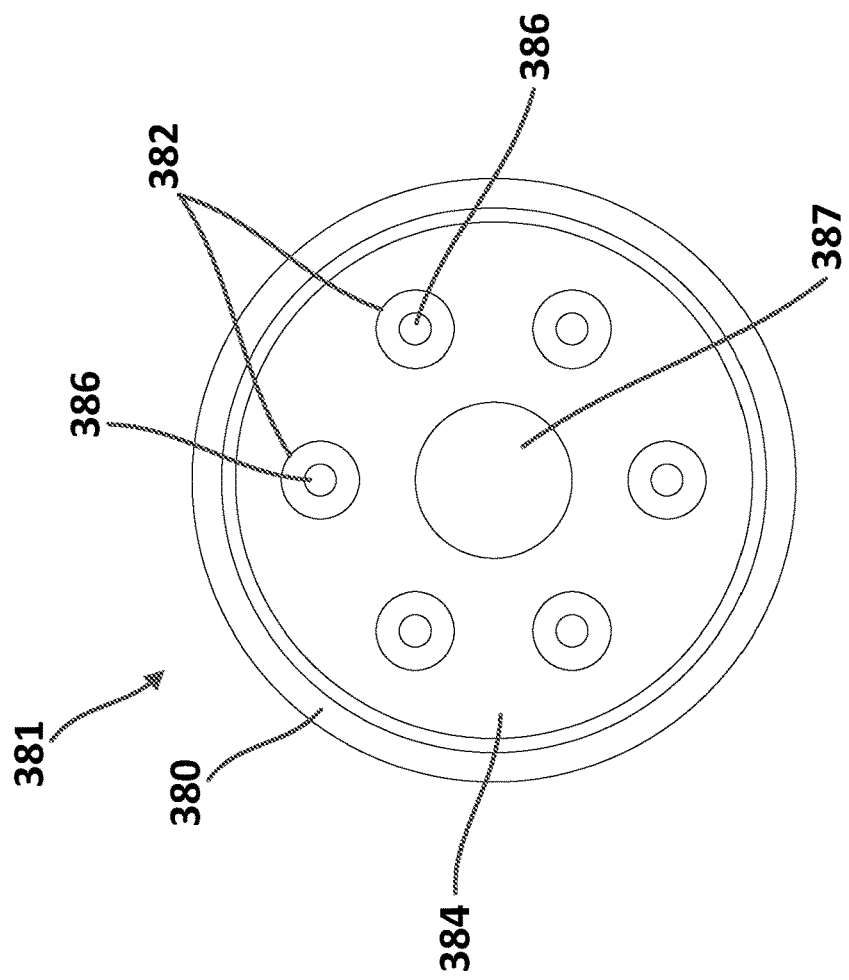
FIG. 15A is a schematic illustration of a distal end view of a delivery device according to an embodiment.

FIGS. 15A and 15B are a distal end view and a side view of a portion of a delivery device 381, respectively, with an inner sheath of the delivery device shown in cross-section in FIG. 15B. The delivery device 381 can be the same or similar in structure and function to the delivery device 181 described above with reference to FIGS. 2A-2D. For example, the delivery device 381 includes an inner sheath 380 axially movable within the lumen of a delivery sheath (not shown). The delivery device 381 also includes suture tubes 382 disposed within and axially moveable relative to the inner sheath 380. Although six suture tubes 382 are shown, any suitable number of suture tubes 382 can be included. Each suture tube 382 can define a suture lumen 386 within which a suture (not shown) can be movably disposed. Each suture tube 382 can be translated along a suture into engagement with a corresponding slip knot (not shown) such that the slip knot is axially movable by the suture tube 382 relative to the suture. In some embodiments, each slip knot is movable by a corresponding suture tube 382 because the inner diameter of each suture tube 382 (i.e., the diameter of each suture lumen 386) at the distal end of each suture tube 382 is less than the diameter of each corresponding slip knot. In other embodiments, each suture tube 382 can include an engagement feature (not shown) capable of engaging with each slip knot for distal and/or proximal translation of each slip knot along each corresponding suture.

A tube positioning member 384 can be coupled to each of the suture tubes 382. As shown in FIGS. 15A and 15B, the tube positioning member 384 can be a sheath within which a frame is secured such that the suture tubes 382 can be attached to the frame. The suture tubes 382 can be fixed to the tube positioning member 384 such that axial movement of the tube positioning member 384 causes simultaneous movement of the suture tubes 382. Additionally, the tube positioning member 384 can define a central lumen 387 such that a tether (not shown) of a valve can be movably disposed within the central lumen 387. In other embodiments, the tube positioning member 384 can be, for example, a sheath within which the suture tubes 382 are securely attached. In other embodiments, the tube positioning member 384 can be a frame securely coupled to each of the suture tubes 382. In some alternative embodiments, the suture tubes 382 can each be controlled independently.

FIG. 16A is a schematic illustration of a delivery device 481 according to an embodiment, shown disposed partially within a delivery sheath 426 (shown in cross-section) during deployment of a prosthetic heart valve 400. FIG. 16A illustrates the prosthetic heart valve 400 in a first configuration, and FIG. 16B illustrates the prosthetic heart valve 400 in a second configuration. The prosthetic heart valve 400 (also referred to herein as "prosthetic valve" or "valve") can be, for example, a prosthetic mitral valve. The valve 400 includes an outer frame 420 and an inner frame 450. The outer frame 420 and the inner frame 450 can each be formed as a tubular structure and in the same or similar manner as described in more detail above for prosthetic valve 100 with reference to FIGS. 1A-2D and prosthetic valve 200 with reference to FIGS. 3-14. The outer frame 420 and the inner frame 450 can be coupled together via sutures 402 as described in more detail below. The valve 400 can also include other features, such as those described with respect to FIGS. 3-14 above. For illustration purposes, only the inner frame 450 and the outer frame 420 are discussed with respect to FIGS. 16A and 16B.

The outer frame 420 is configured to have a biased expanded or undeformed shape and can be manipulated and/or deformed (e.g., compressed or constrained) and, when released, return to its original (expanded or undeformed) shape. For example, the outer frame 420 can be formed of materials, such as metals or plastics, having shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 450 can be formed from a laser-cut tube of Nitinol®. The inner frame 450 can also have a biased expanded or undeformed shape and can be manipulated and/or deformed (e.g., compressed and/or constrained) and, when released, return to its original (expanded or undeformed) shape. Further details regarding the inner frame 450 and the outer frame 420 are described above with respect to valve 200 and FIGS. 3-14.

More specifically, the valve 400 can have a biased expanded configuration as shown in FIG. 16A (similar to valve 100 as shown in FIGS. 2B and 2C) and a compressed or collapsed configuration (similar to valve 100 as shown in FIGS. 1A, 1B, and 2A). The expanded configuration allows the valve 400 to function when implanted within the heart. The valve 400 can be moved to the compressed or collapsed configuration for delivery of the valve 400 to the heart of a patient. As described above for previous embodiments, the valve 400 can be delivered and deployed within a heart using a variety of different delivery approaches including, for example, a transfemoral delivery approach, a transatrial approach, a transapical approach, or a transjugular approach.

Similarly as described above with respect to valve 100 and shown in FIG. 1A, the valve 400 can be delivered to the heart of a patient using a delivery system that includes the delivery sheath 426 and the delivery device 481. Although not shown with reference to FIGS. 16A and 16B, the valve 400 can be disposed within a lumen 427 of the delivery sheath 426 in an axially extended configuration. More specifically, the valve 400 can be disposed within the lumen 427 of the delivery sheath 426 with the inner frame 450 disposed axially distally of the outer frame 420. In some embodiments, the inner frame 450 can be entirely disposed distally of a distal end of the outer frame 420. In other words, the inner frame 450 is disposed at a non-zero distance from the outer frame 420. In other embodiments, the inner frame 450 can be disposed such that a portion of the inner frame 450 is within the outer frame 420, but the inner frame 450 is not within the outer frame 420 to the same extent as when the inner frame 450 is nested within the outer frame 420 when the valve 400 is fully assembled. The inner frame 450 can be coupled to the outer frame 420 via the sutures 402. When the valve 400 is in the axially extended configuration (e.g., first configuration), the sutures 402 extend from the inner frame 450 to the outer frame 420 and then proximally from the outer frame into the delivery device 481 as described in more detail below.

With the valve 400 in the axially extended configuration, the valve 400 can be placed within the lumen 427 of the delivery sheath 426 (similar to valve 100 as shown in FIG. 1A) for delivery of the valve 400 to the heart (e.g., the left atrium of the heart). When placed within the lumen of the delivery sheath 426, the valve 400 can be moved to the collapsed or compressed configuration in which the outer diameter or outer perimeter of the valve 400 is reduced. Said another way, the outer frame 420 and the inner frame 450 are each moved to a collapsed or compressed configuration in which the outer diameter of each of the outer frame 420 and the inner frame 450 is reduced.

Thus, by disposing the outer frame 420 and the inner frame 450 in the axially extended configuration, the valve 400 can be collapsed into a smaller overall diameter, i.e. placed in a smaller diameter delivery sheath 426, than would be possible if the outer frame 420 and the inner frame 450 of the valve 400 were merely nested and collapsed radially. As described above, when the inner frame 450 is nested within an interior of the outer frame 420, the outer frame 420 must be collapsed around the inner frame 450. In some embodiments, the inner frame 450 and the outer frame 420 are disposed concentrically when nested together. In the axially extended configuration, the inner frame 450 and the outer frame 420 are arranged axially with respect to each other (i.e., the inner frame is not nested or is only partially nested within the outer frame 420), such that the outer frame 420 can be collapsed without needing to accommodate all of the structure of the inner frame 450 inside the outer frame 420. In other words, with the inner frame 450 disposed mostly inside or nested within the outer frame 420, the layers or bulk of the frame structures cannot be compressed to as small a diameter. In addition, if the frames are nested, the structure is less flexible, and therefore, more force is needed to bend the valve, e.g., to pass through tortuous vasculature or to make tight turns in, for example, the left atrium after passing through the atrial septum to be properly oriented for insertion into the mitral valve annulus.

The outer frame 420 and the inner frame 450 can be coupled via the sutures 402.

Although two sutures 402 are shown, any suitable number of sutures 402 can be used to couple the outer frame 420 to the inner frame 450. The sutures 402 can be securely attached to the inner frame 450 via any suitable method. Additionally, the outer frame 420 can include apertures 422 within which the sutures 402 can be movably disposed. In some embodiments, each aperture 422 can be aligned with an attachment location of a suture 402 to the inner frame 450. Each of the sutures 402 includes and/or is coupled to a slip knot 404 which is movable along each suture 402. The sutures 402 and slip knots 404 can be used to move the valve 400 to the nested configuration as described in more detail below. In some embodiments, the sutures 402 can be pulled proximally such that the inner frame 450 is pulled proximally into the nested configuration. The slip knots 404 can then be translated along the sutures 402 toward the valve 400 such that the outer frame 420 is secured to the inner frame 450. For example, in some embodiments, the apertures 422 in the outer frame 420 can be smaller in diameter than the diameter of the slip knots 404, such that the outer frame 420 cannot move proximally beyond the location of the slip knots 404. Additionally, in some embodiments, the distal end of the delivery sheath 426 can act as a stop (i.e., limit proximal movement of the valve 400). Said another way, as the sutures 402 are pulled proximally, the valve 400 cannot be pulled proximally beyond the distal end of the delivery sheath 426 (i.e., into the delivery sheath 426).

The delivery device 481 includes an inner sheath 480 axially movable within the lumen 427 of the delivery sheath 426. Suture tubes 482 can be disposed within the inner sheath 480 and can be axially movable relative to the inner sheath 480. Each suture tube 482 can define a suture lumen (not shown) within which a suture 402 can be movably disposed. Each suture tube 482 can be translated along a suture 402 and engage with a corresponding slip knot 404 such that the slip knot 404 is axially movable by the suture tube 482 relative to the suture 402. In some embodiments, each slip knot 404 is movable by each suture tube 482 because the inner diameter of each suture tube 482 (i.e., the diameter of each suture lumen) at the distal end of each suture tube 482 is less than the diameter of each corresponding slip knot 404. In other embodiments, each suture tube 482 can include an engagement feature (not shown) capable of engaging with each slip knot 404 for distal and/or proximal translation of each slip knot 404 along each corresponding suture 402. Although two suture tubes 482 are shown in FIG. 16A, any suitable number of suture tubes 482 can be used. For example, in some embodiments, the number of suture tubes 482 can be equal to the number of sutures 402. In other embodiments, the number of suture tubes 482 can be greater than or less than the number of sutures 402.

A tube positioning member (not shown) can be coupled to each of the suture tubes 482. As described above for previous embodiments, the tube positioning member can be, for example, a sheath within which the suture tubes 482 are securely attached. In other embodiments, the tube positioning member can be a frame securely coupled to each of the suture tubes 482. In other embodiments, the tube positioning member can be a sheath within which a frame is secured such that the suture tubes 482 can be attached to the frame. Additionally, the tube positioning member can define a central lumen (not shown) such that a tether 492 (FIG. 16B)

coupled to and extending from the valve 400 can be disposed therein. The suture tubes 482 can be fixed to the tube positioning member such that axial movement of the tube positioning member causes simultaneous movement of the suture tubes 482. In alternative embodiments, the suture tubes 482 can each be controlled independently.

FIG. 16A shows the valve 400 after the valve 400 has been moved out of the distal end of the delivery sheath 426 and into an expanded configuration. In some embodiments, the inner sheath 480 can engage with the valve 400 to control the position of the valve 400 relative to the delivery sheath 426 and control the sequential delivery of the inner frame 450 and the outer frame 420 from the delivery sheath 426. In such embodiments, the inner sheath 480 can push the outer frame 420 distally into abutting contact with the inner frame 450. Further distal movement of the inner sheath 480 can cause the outer frame 420 to push the inner frame 450 distally such that the inner frame 450 is pushed from the distal end of the delivery sheath 426. The inner sheath 480 can continue to push the outer frame 420 distally until the outer frame 420 is also pushed distally of the distal end of the delivery sheath 426. In other embodiments, another component (not shown) can be used similarly to push the valve 400 distally such that the inner frame 450 and the outer frame 420 are sequentially delivered from the delivery sheath 426. Alternatively, the inner sheath 480 or another component (not shown) can prevent proximal movement of the valve 400 while the delivery sheath 426 is retracted relative to the valve 400 such that the inner frame 450 and the outer frame 420 can sequentially transition into their expanded configurations.

As shown in FIG. 16A, after the valve 400 has been moved from the distal end of the delivery sheath 426, the inner frame 450 is still axially extended relative to the outer frame 420. Before the inner frame 450 is pulled into the nested configuration, the inner sheath 480 can be pushed distally such that the inner sheath 480 extends from the distal end of the delivery sheath 426. The suture tubes 482 can then be pushed distally along the sutures 402 such that the suture tubes 482 extend distally of the distal end of the inner sheath 480. Although the inner sheath 480 is described as being extended distally of the delivery sheath 426 prior to extending the suture tubes 482 from the inner sheath 480, in some embodiments the inner sheath 480 can remain within the delivery sheath 426 and/or not be moved within the delivery sheath 426 during the deployment of the suture tubes 482 along the sutures 402 from the distal end of the inner sheath 480.

The sutures 402 can then be pulled proximally through the suture tubes 482 while the slip knots 404 are held stationary by the distal end of the suture tubes 482 such that the inner frame 450 is moved proximally into a nested position within the outer frame 420. The suture tubes 482 can be distally translated along the sutures 402 such that each slip knot 404 is moved distally along the sutures 402 by the distal end of a suture tube 482 until the slip knots 404 are pushed into contact with the outer frame 420 and the inner frame 450 and the outer frame 420 are secured relative to each other. In some embodiments, the distal movement of the slip knots 404 via distal movement of the suture tubes 482 can occur simultaneously while the sutures 402 are pulled proximally. As shown in FIG. 16B, when the inner frame 450 and the outer frame 420 are properly positioned relative to each other (e.g., in the nested configuration), the sutures 402 can be severed proximally of the location of the slip knots 404 and the portion of sutures 402 proximal of the severance can be removed. In some embodiments, the suture tubes 482 can each include a cutting feature (not shown) for separation and removal of a portion of each suture 402 proximal of each slip knot 404. In some embodiments, after the inner frame 450 and the outer frame 420 are secured to each other, the tether 492 attached to the valve 400 can be used to position the valve 400 in the native annulus. For example, the tether 492 can be coupled to the inner frame 450 prior to delivery of the valve 400 to the left atrium. Once the valve 400 is positioned in the left atrium, the tether can be pulled proximally such that the valve 400 is seated in the native annulus.

In some embodiments, the tether 492 can be pulled proximally to pull the inner frame 450 into the nested position within the outer frame 420. The tether 492 can be used to pull the inner frame 450 either in the alternative or in addition to the sutures 402. In embodiments where the tether 492 is used to position the inner frame 450 relative to the outer frame 420 in addition to the sutures 402, the tether 492 and the sutures 402 can be pulled simultaneously, or sequentially, to position the inner frame 450 relative to the outer frame 420.

In some alternative embodiments, the outer frame 420 can be only partially delivered before the inner frame 450 is pulled proximally into a partial or fully nested position as described above with respect to FIG. 2D. In such embodiments, the inner frame 450 can be delivered from the distal end of the delivery sheath 426 similarly as described above with reference to FIG. 16A. For example, the inner sheath 480 can engage with the valve 400 to control the sequential delivery of the inner frame 450 and the outer frame 420 from the delivery sheath 426. The inner sheath 480 can push the outer frame 420 distally into abutting contact with the inner frame 450. Further distal movement of the inner sheath 480 can cause the outer frame 420 to push the inner frame 450 distally such that the inner frame 450 is pushed from the distal end of the delivery sheath 426. The inner sheath 480 can continue to push the outer frame 420 distally such that the outer frame 420 begins to transition to the expanded configuration as it is partially deployed from the distal end of the delivery sheath 426. With the outer frame in a partially deployed configuration at the distal end of the delivery sheath 426, the inner frame 450 is in a biased expanded configuration and the inner frame 450 is still axially disposed relative to the outer frame 420.

With the outer frame 420 in the partially deployed position, the sutures 402 can be pulled proximally through the suture tubes 482 while the outer frame 420 is held stationary at the distal end of the delivery sheath 426 such that the inner frame 450 is moved proximally into a partially nested position within the outer frame 420. After the inner frame 450 is partially nested within the outer frame 420 and when the outer frame 420 is in the partially deployed position, the slip knots 404 can be pushed distally along at least a portion of the sutures 402 by the suture tubes 482. The outer frame 420 can then be pushed distally into the fully expanded, fully deployed configuration. For example, in some embodiments, the inner sheath 480 can continue to push the outer frame 420 distally until the outer frame 420 is pushed distally of the distal end of the delivery sheath 426. While the outer frame 420 is being pushed distally from the delivery sheath 426 and/or after the outer frame 420 has been moved to the expanded configuration, the sutures 402 can be pulled further proximally such that the inner frame 450 is moved to a fully nested position within the outer frame 420. The slip knots 404 can be moved to the position shown in FIG. 16B by the suture tubes 482 such that the position of the inner frame 450 relative to the outer frame 420 is secured by the slip knots 404, as described above with reference to FIG. 16B.

Figure 17:
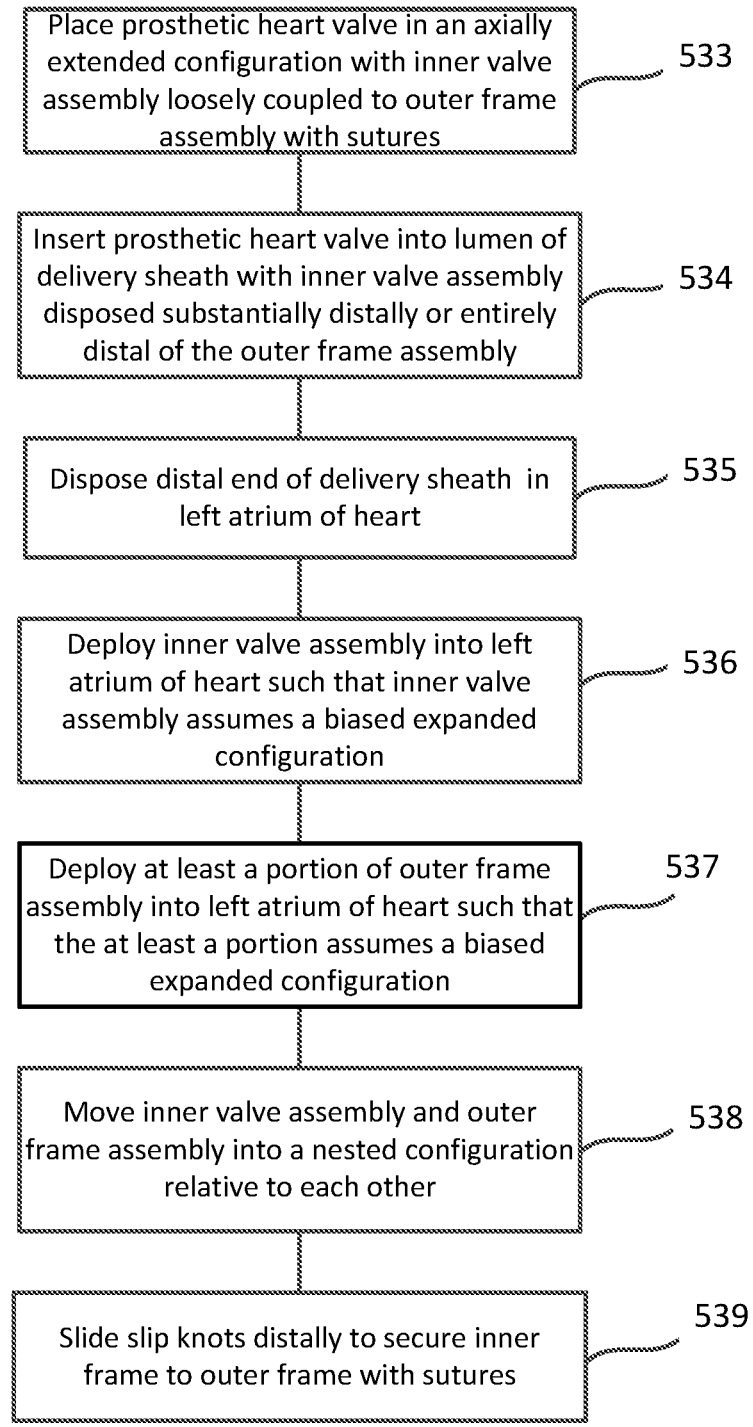
FIG. 17 is a flowchart of a method of delivering and deploying a prosthetic heart valve within a heart of a patient.

FIG. 17 is a flowchart of a method of delivering and deploying a prosthetic heart valve (e.g., a prosthetic mitral valve) within a heart of a patient. At 533, a prosthetic heart valve (e.g., a prosthetic mitral valve) is placed in an axially extended configuration in which the inner valve assembly and the outer frame assembly are disposed in an axial relation to each other. For example, as described above, the inner valve assembly can be disposed at a spaced or non-zero distance from the outer frame assembly, or can be disposed substantially distally of the outer frame assembly (substantially not overlapping, or partially overlapping). The inner valve assembly and the outer frame assembly can be loosely coupled together with sutures. At 534, the prosthetic heart valve is placed within a lumen of a delivery sheath such that the inner valve assembly and the outer frame assembly are moved to a collapsed configuration and the inner valve assembly is disposed substantially distally of the outer frame assembly or entirely distal of the outer frame assembly in the axially extended configuration. At 535, a distal end portion of the delivery sheath can be disposed within the left atrium of a heart. For example, in some embodiments, the delivery sheath can be delivered via a transapical approach through a puncture site at an apex region of the heart, through the left ventricle and into the left atrium. At 536, the inner valve assembly can be deployed outside a distal end of the delivery sheath and within the left atrium such that the inner valve assembly assumes a biased expanded configuration. At 537, the outer frame assembly can be at least partially deployed within the left atrium such that the portion deployed can assume an expanded configuration. For example, as discussed above, in some embodiments, the outer frame assembly can be fully deployed outside of the delivery sheath and within the left atrium and in some embodiments, the outer frame assembly can be only partially deployed. At 538, the inner valve assembly and the outer frame assembly can be moved relative to each other into a nested configuration. At 539, slip knots can be moved distally to secure the outer frame assembly to the inner valve assembly. With the inner valve assembly and the outer frame assembly secured together, the sutures extending from the slip knots can be cut, and the prosthetic valve can be positioned within the native mitral annulus of the heart. A tether coupled to the prosthetic valve can be tensioned, and then secured to the apex of the heart with an epicardial pad device.

In some embodiments, the suture tails from the sutures used to couple the outer frame assembly to the inner valve assembly can be snared with a snare device. The snare device can be used to capture or snare the suture tails extending from the slip knots and pull the suture tails into, for example, a delivery tube or sheath. The suture tails could be snared individually in separate tubes, in groups, or all in a single tube. The snaring could be accomplished at the same time that the leader/tether tube is snared and routed through the device as described, for example, in the '305 PCT application incorporated by reference above.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

For example, although not specifically described with reference to specific embodiments, the prosthetic heart valves described herein can be secured to a heart using an epicardial pad device as described, for example, in International Application No. PCT/US2016/012305, entitled "Prosthetic Mitral Valves and Apparatus and Methods for Delivery of Same," incorporated by reference above. Additionally, although embodiments described herein include slip knots for securing an inner frame to an outer frame (e.g., slip knots 404 for securing the inner frame 450 to the outer frame 420 shown in FIG. 16B), in some alternative embodiments an outer frame can include a snap fit mechanism for engagement with an inner frame. For example, a snap fit mechanism can be located on the distal end of an outer frame, such as outer frame 420. When an inner frame (e.g., inner frame 450), is pulled via proximal movement of associated sutures and/or a tether (e.g., sutures 402 and/or tether 492), the inner frame can be pulled into the nested position relative to the outer frame and retained in the nested position relative to the outer frame by the snap fit mechanism. When retained in the nested position, the inner frame cannot move distally out of the nested position.

Further, although not shown, any of the embodiments of a delivery device or system can include a handle or handle assembly to which the various delivery sheaths and components can be operatively coupled and which a user (e.g., physician) can grasp and use to manipulate the delivery device or system.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein.

What is claimed is:

1. An apparatus, comprising:
   a delivery device including a sheath having a distal end and a proximal end;
   a prosthetic heart valve including an inner frame securing a valve assembly and an outer frame coupleable to the inner frame via at least one suture,
   the inner frame and the outer frame moveable relative to each other between a first position in which the inner frame and the outer frame are disposed within the sheath such that the outer frame is substantially axially proximal of the inner frame and a second position in which the inner frame is nested substantially within an interior portion of the outer frame,
   the prosthetic valve movable between a first configuration for delivery into a heart of a patient and a second configuration when the inner frame and the outer frame have been deployed from the sheath, the prosthetic valve being in the first configuration when the inner frame and the outer frame are in the first position relative to each other, the prosthetic valve being in the second configuration when the inner frame and the outer frame are in the second position relative to each other.

2. The apparatus of claim 1, wherein the at least one suture includes a slip knot that can be moved relative to the at least one suture to secure the outer frame to the inner frame when the prosthetic heart valve is in the second configuration.

3. The apparatus of claim 1, wherein the at least one suture includes a plurality of sutures, each suture from the plurality of sutures coupled to the inner frame and extending proximally through openings in the outer frame and extending proximally from the outer frame.

4. The apparatus of claim 1, wherein the at least one suture includes a plurality of sutures, each suture from the plurality of sutures coupled to the inner frame and extending proximally through openings in the outer frame and extending proximally from the outer frame, and each suture from the plurality of sutures including a slip knot disposed proximally of the outer frame.

5. The apparatus of claim 1, wherein when the inner frame and the outer frame are in the first position relative to each other the outer frame is disposed at a non-zero distance from the inner frame.

6. A method, comprising:
inserting into a heart of a patient, a prosthetic heart valve that includes an inner frame securing a valve assembly and an outer frame coupleable to the inner frame via at least one suture, during the inserting the inner frame and the outer frame are disposed within a delivery sheath in a collapsed configuration and the outer frame is positioned at least partially axially proximal of the inner frame;
deploying the prosthetic heart valve within the heart such that the inner frame is moved to an expanded configuration within the heart and the outer frame is at least partially moved to an expanded configuration within the heart,
after the deploying, moving the outer frame and the inner frame relative to each other into a nested configuration in which the inner frame is disposed substantially within an interior portion of the outer frame.

7. The method of claim 6, further comprising:
after the moving of the outer frame and the inner frame into the nested configuration, securing the inner frame to the outer frame with the at least one suture.

8. The method of claim 6, further comprising:
after the moving of the outer frame and the inner frame into the nested configuration, securing the inner frame to the outer frame with the at least one suture comprising a slip knot.

9. The method of claim 6, wherein the moving of the outer frame and the inner frame into the nested configuration includes sliding a slip knot distally along the at least one suture while pulling proximally the at least one suture such that the inner frame and outer frame are moved relative to each other and the inner frame is disposed substantially within the interior portion of the outer frame.

10. The method of claim 7, further comprising:
inserting a positioning member into the lumen of the delivery sheath, the positioning member including at least one suture tube defining a lumen; and
disposing the at least one suture at least partially within a lumen of a suture tube of the at least one suture tubes;
the moving of the outer frame and the inner frame relative to each other into the nested configuration includes moving a slip knot distally along the at least one suture using the positioning member while pulling proximally the at least one suture such that the inner frame and outer frame are moved relative to each other and the inner frame is disposed substantially within the interior portion of the outer frame.

11. The method of claim 10, further comprising:
inserting a snare device into a lumen of a suture tube from the at least one suture tube, the disposing the at least one suture at least partially within the lumen of the suture tube of the at least one suture tubes includes snaring the at least one suture with the snare device and pulling the at least one suture proximally within the lumen of the suture tube.

12. The method of claim 7, wherein the inserting the prosthetic heart valve includes inserting a distal end portion of the delivery sheath into the left atrium of the heart, the method further comprising:
with the prosthetic heart valve in the second configuration, positioning the prosthetic heart valve within a mitral annulus of the heart in a desired orientation.

13. The method of claim 10, further comprising:
with the inner frame and the outer frame in the nested configuration, positioning the prosthetic heart valve within the mitral annulus of the heart in a desired orientation; and
cutting the at least one suture proximally of the slip knot.

14. The method of claim 6, wherein the deploying the prosthetic heart valve within the heart includes deploying the inner frame and outer frame sequentially.

15. The method of claim 6, wherein the deploying the prosthetic heart valve within the heart includes deploying the inner frame and outer frame substantially simultaneously.

16. A method, comprising:
inserting a prosthetic heart valve into a lumen of a delivery sheath, the prosthetic heart valve including an inner valve assembly and an outer frame assembly coupleable to the inner valve assembly via at least one suture, the prosthetic heart valve being inserted into the lumen of the delivery sheath with the inner valve assembly disposed at least partially distally of the outer frame assembly;
disposing a distal end portion of the delivery sheath in a left atrium of a heart;
deploying the inner valve assembly into the left atrium of the heart such that the inner valve assembly assumes a biased expanded configuration;
deploying at least a portion of the outer frame assembly into the left atrium of the heart such that the at least a portion of the outer frame assembly assumes a biased expanded configuration;
moving the inner valve assembly and the outer frame assembly into a nested configuration in which the inner valve assembly is at least partially disposed within a portion of the outer frame assembly;
securing the inner valve assembly to the outer frame assembly with the at least one suture; and
positioning, after the securing, the prosthetic heart valve within a native annulus of the heart in a desired orientation.

17. The method of claim 16, further comprising:
prior to the inserting the prosthetic heart valve into the lumen of the delivery sheath, placing the prosthetic heart valve in an axially extended configuration in which the inner valve is loosely coupled to the outer valve with the at least one suture.

18. The method of claim 16, wherein the moving the inner valve assembly and the outer frame assembly into the nested configuration includes moving distally at least one slip knot along the at least one suture while pulling proximally the at least one suture.

19. The method of claim 16, wherein the deploying at least a portion of the outer frame assembly includes deploying the entire outer frame assembly such that the outer frame assembly assumes a biased expanded configuration.

20. The method of claim 16, further comprising:
inserting a positioning member into the lumen of the delivery sheath, the positioning member including at least one suture tube; and
disposing the at least one suture at least partially within a lumen of a suture tube of the at least one suture tubes;
the moving the inner valve assembly and the outer frame assembly into theft nested configuration includes moving a slip knot distally along the at least one suture using the positioning member while pulling proximally the at least one suture such that the inner frame and outer frame are moved relative to each other and the inner frame is at least partially disposed within an interior of the outer frame assembly.

21. The method of claim 20, further comprising:
inserting a snare device into the lumen of the suture tube from the at least one suture tubes, the disposing the at least one suture at least partially within the lumen of the suture tube of the at least one suture tubes includes snaring the at least one suture with the snare device and pulling the at least one suture proximally within the lumen of the suture tube.

22. The method of claim 16, wherein the positioning comprises positioning the prosthetic heart valve within the mitral annulus of the heart in a desired orientation.

23. The method of claim 20, further comprising:
cutting the at least one suture proximally of the slip knot.

* * * * *

UNITED STATES PATENT AND TRADEMARK OFFICE
CERTIFICATE OF CORRECTION

PATENT NO. : 11,039,921 B2
APPLICATION NO. : 16/305113
DATED : June 22, 2021
INVENTOR(S) : Zachary J. Tegels Page 1 of 1

It is certified that error appears in the above-identified patent and that said Letters Patent is hereby corrected as shown below:

On the Title Page

Please correct item (86) shown below:
(86) PCT No.: "PCT/US2017/736949" should read --PCT/US2017/36949--.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*